(12) United States Patent
Burgey et al.

(10) Patent No.: US 7,632,832 B2
(45) Date of Patent: Dec. 15, 2009

(54) CGRP RECEPTOR ANTAGONISTS

(75) Inventors: Christopher S. Burgey, Philadelphia, PA (US); Theresa M. Williams, Harleysville, PA (US); Zhengwu J. Deng, Eagleville, PA (US); Craig A. Stump, Pottstown, PA (US)

(73) Assignee: Merck & Co., Inc., Rahway, NJ (US)

( * ) Notice: Subject to any disclaimer, the term of this patent is extended or adjusted under 35 U.S.C. 154(b) by 140 days.

(21) Appl. No.: 11/795,678

(22) PCT Filed: Jan. 13, 2006

(86) PCT No.: PCT/US2006/001252

§ 371 (c)(1),
(2), (4) Date: Jul. 18, 2007

(87) PCT Pub. No.: WO2006/078554

PCT Pub. Date: Jul. 27, 2006

(65) Prior Publication Data

US 2008/0125413 A1    May 29, 2008

Related U.S. Application Data

(60) Provisional application No. 60/644,650, filed on Jan. 18, 2005.

(51) Int. Cl.
*C07D 401/14*   (2006.01)
*A61K 31/4745*  (2006.01)
*A61P 25/06*    (2006.01)

(52) U.S. Cl. .................. 514/221; 540/509; 540/512

(58) Field of Classification Search .................. 540/509, 540/512; 514/221
See application file for complete search history.

(56) References Cited

FOREIGN PATENT DOCUMENTS

WO      WO 00/18764      4/2000

OTHER PUBLICATIONS

Mar. 17, 2009 Search Report for counterpart EPO Application No. 06718339.2.

*Primary Examiner*—Bruck Kifle
(74) *Attorney, Agent, or Firm*—John C. Todaro; William Krovatin

(57) ABSTRACT

Compounds of Formula I: (where variables R1, R2, R3, R7, G, J, Q, T, W, X and Y are as defined herein) useful as antagonists of CGRP receptors and useful in the treatment or prevention of diseases in which the CGRP is involved, such as headache, migraine and cluster headache, and pharmaceutical compositions comprising these compounds and the use of these compounds and compositions in the prevention or treatment of such diseases in which CGRP is involved.

(I)

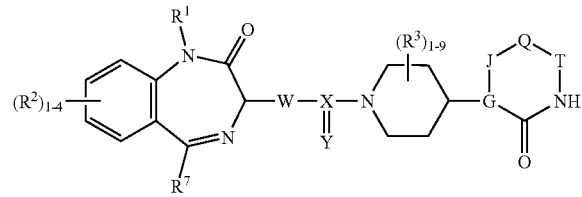

6 Claims, No Drawings

CGRP RECEPTOR ANTAGONISTS

RELATED APPLICATION DATA

This is a National filing under 35 USC 371 of PCT/US2006/001252filed Jan. 13, 2006, which claims priority from U.S. Ser. No. 60/644,650, filed Jan. 18, 2005.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted CGRP1 and CGRP2. Human-CGRP-(8-37), a fragment of CGRP that lacks seven N-terminal amino acid residues, is a selective antagonist of CGRP1, whereas the linear analogue of CGRP, diacetoamido methyl cysteine CGRP ([Cys(ACM)2,7] CGRP), is a selective agonist of CGRP2. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purinies and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., hit. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyper-reactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of Formula I:

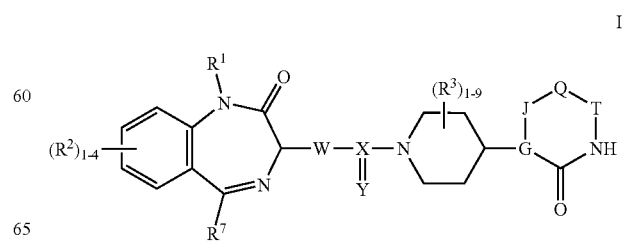

(where variables R1, R2, R3, R7, G, J, Q, T, W, X and Y are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to CGRP antagonists which include compounds of Formula I:

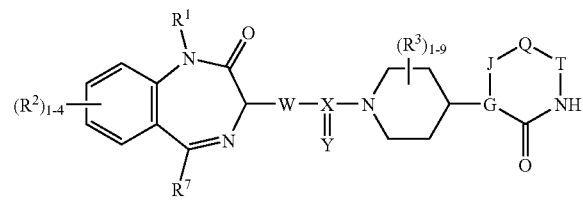

wherein:
R1 is selected from:
1) H, C1-C6 alkyl, C2-C6 alkenyl, C2-C6 alkynyl, C3-6 cycloalkyl, and heterocycle, unsubstituted or substituted with one or more substituents independently selected from:
   a) C1-6 alkyl,
   b) C3-6 cycloalkyl,
   c) aryl, unsubstituted or substituted with 1-5 substituents where the substituents are independently selected from R4,
   d) heteroaryl, unsubstituted or substituted with 1-5 substituents independently selected from R4,
   e) heterocycle, unsubstituted or substituted with 1-5 substituents independently selected from R4,
   f) (F)pC1-3 alkyl,
   g) halogen,
   h) OR4,
   i) O(CH2)s OR4,
   j) CO2R4,
   k) (CO)NR10R11,
   l) O(CO)NR10R11,
   m) N(R4)(CO)NR10R11,
   n) N(R10)(CO)R11,
   o) N(R10)(CO)OR11,
   p) SO2NR10R11,
   q) N(R10) SO2R11,
   r) S(O)mR10,
   s) CN,
   t) NR10R11,
   u) N(R10)(CO)NR4R11, and
   v) O(CO)R4; and
2) aryl or heteroaryl, unsubstituted or substituted with one or more substituents independently selected from:
   a) C1-6 alkyl,
   b) C3-6 cycloalkyl,
   c) aryl, unsubstituted or substituted with 1-5 substituents where the substituents are independently selected from R4,
   d) heteroaryl, unsubstituted or substituted with 1-5 substituents independently selected from R4,
   e) heterocycle, unsubstituted or substituted with 1-5 substituents independently selected from R4,
   f) (F)pC1-3 alkyl,
   g) halogen,
   h) OR4,
   i) O(CH2)sOR4,
   j) CO2R4,
   k) (CO)NR10R11,
   l) O(CO)NR10R11,
   m) N(R4)(CO)NR10R11,
   n) N(R10)(CO)R11,
   o) N(R10)(CO)OR11,
   p) SO2NR10R11,
   q) N(R10) SO2R11,
   r) S(O)mR10,
   s) CN,
   t) NR10R11,
   u) N(R10)(CO)NR4R11, and
   v) O(CO)R4; and
R2 is independently selected from H and:
   1) C1-6 alkyl,
   2) C3-6 cycloalkyl,
   3) aryl, unsubstituted or substituted with 1-5 substituents independently selected from R4,
   4) heteroaryl, unsubstituted or substituted with 1-5 substituents independently selected from R4,
   5) heterocycle, unsubstituted or substituted with 1-5 substituents independently selected from R4,
   6) (F)pC1-3 alkyl,
   7) halogen,
   8) OR4,
   9) O(CH2)sOR4,
   10) CO2R4,
   11) (CO)NR10R11,
   12) O(CO)NR10R11,
   13) N(R4)(CO)NR10R11,
   14) N(R10)(CO)R11,
   15) N(R10)(CO)OR11,
   16) SO2NR10R11,
   17) N(R10) SO2R11,
   18) S(O)mR10,
   19) CN,
   20) NR10R11,
   21) N(R10)(CO)NR4R11, and
   22) O(CO)R4;
R7 is selected from:
1) H, C0-C6 alkyl, C2-C6 alkenyl, C2-C6 alkynyl, C3-6 cycloalkyl and heterocycle, unsubstituted or substituted with one or more substituents independently selected from:
   a) C1-6 alkyl,
   b) C3-6 cycloalkyl,
   c) aryl, unsubstituted or substituted with 1-5 substituents where the substituents are independently selected from R4,
   d) heteroaryl, unsubstituted or substituted with 1-5 substituents independently selected from R4,
   e) heterocycle, unsubstituted or substituted with 1-5 substituents independently selected from R4,
   f) (F)pC1-3 alkyl,
   g) halogen,
   h) OR4,
   i) O(CH2)sOR4,
   j) CO2R4,
   k) (CO)NR10R11,
   l) O(CO)NR10R11,
   m) N(R4)(CO)NR10R11, n) N(R10)(CO)R11,
o) N(R10)(CO)OR11,
p) SO2NR10R11,
q) N(R10) SO2R11,
r) S(O)mR10,
s) CN,
t) NR10R11,
u) N(R10)(CO)NR4R11,
v) O(CO)R4; and 2) aryl or heteroaryl, unsubstituted or substituted with one or more substituents independently selected from:
   a) C1-6 alkyl,
   b) C3-6 cycloalkyl,
   c) aryl, unsubstituted or substituted with 1-5 substituents where the substituents are independently selected from R4,
   d) heteroaryl, unsubstituted or substituted with 1-5 substituents independently selected from R4,
   e) heterocycle, unsubstituted or substituted with 1-5 substituents independently selected from R4,
   f) (F)pC1-3 alkyl,
   g) halogen,
   h) OR4,
   i) O(CH2)sOR4,
   j) CO2R4,
   k) (CO)NR10R11,
   l) O(CO)NR10R11,
   m) N(R4)(CO)NR10R11,
   n) N(R10)(CO)R11,
   o) N(R10)(CO)OR11,
   p) SO2NR10R11,
   q) N(R10) SO2R11,
   r) S(O)mR10,
   s) CN,
   t) NR10R11,
   u) N(R10)(CO)NR4R11, and
   v) O(CO)R4;

R10 and R11 are independently selected from: H, C1-6 alkyl, (F)pC1-6 alkyl, C3-6 cycloalkyl, aryl, heteroaryl, and benzyl, unsubstituted or substituted with halogen, hydroxy or C1-C6 alkoxy, where R10 and R11 may be joined together to form a ring selected from: azetidinyl, pyrrolidinyl, piperidinyl, piperazinyl, or morpholinyl, which is unsubstituted or substituted with 1-5 substituents independently selected from R4;

R4 is independently selected from: H, C1-6 alkyl, (F)pC1-6 alkyl, C3-6 cycloalkyl, aryl, heteroaryl and benzyl, unsubstituted or substituted with halogen, hydroxy or C1-C6 alkoxy;

W is O, NR4 or C(R4)$_2$;

X is C or S;

Y is O, (R4)$_2$, NCN, NSO2CH3 or NCONH2, or Y is O2 when X is S;

R5 is independently selected from H and:

1) C1-C6 alkyl, C2-C6 alkenyl, C2-C6 alkynyl, C3-6 cycloalkyl and heterocycle, unsubstituted or substituted with one or more substituents independently selected from:
   a) C1-6 alkyl,
   b) C3-6 cycloalkyl,
   c) aryl, unsubstituted or substituted with 1-5 substituents where the substituents are independently selected from R4,
   d) heteroaryl, unsubstituted or substituted with 1-5 substituents independently selected from R4,
   e) heterocycle, unsubstituted or substituted with 1-5 substituents independently selected from R4,
   f) (F)pC1-3 alkyl,
   g) halogen,
   h) OR4,
   i) O(CH2)sOR4,
   j) CO2R4,
   k) (CO)NR10R1,
   l) O(CO)NR10R11,
   m) N(R4)(CO)NR10R11,
   n) N(R10)(CO)R11,
   o) N(R10)(CO)OR11,
   p) SO2NR10R11,
   q) N(R10) SO2R11,
   r) S(O)mR10,
   s) CN,
   t) NR10R11,
   u) N(R10)(CO)NR4R11, and
   v) O(CO)R4;

2) aryl or heteroaryl, unsubstituted or substituted with one or more substituents independently selected from:
   a) C1-6 alkyl,
   b) C3-6 cycloalkyl,
   c) aryl, unsubstituted or substituted with 1-5 substituents where the substituents are independently selected from R4,
   d) heteroaryl, unsubstituted or substituted with 1-5 substituents independently selected from R4,
   e) heterocycle, unsubstituted or substituted with 1-5 substituents independently selected from R4,
   f) (F)pC1-3 alkyl,
   g) halogen,
   h) OR4,
   i) O(CH2)sOR4,
   j) CO2R4,
   k) (CO)NR10R11,
   l) O(CO)NR10R11,
   m) N(R4)(CO)NR10R11,
   n) N(R10)(CO)R11,
   o) N(R10)(CO)OR11,
   p) SO2NR10R11,
   q) N(R10) SO2R11,
   r) S(O)mR10,
   s) CN,
   t) NR10R11,
   u) N(R10)(CO)NR4R11, and
   v) O(CO)R4;

3) C1-6 alkyl,
4) C3-6 cycloalkyl,
5) heterocycle, unsubstituted or substituted with 1-5 substituents independently selected from R4,
6) (F)pC1-3 alkyl,
7) halogen,
8) OR4,
9) O(CH2)sOR4,
10) CO2R4,
11) (CO)NR10R11,
12) O(CO)NR10R11,
13) N(R4)(CO)NR10R11,
14) N(R10)(CO)R11,
15) N(R10)(CO)OR11,
16) SO2NR10R11,
17) N(R10) SO2R11,
18) S(O)mR10,
19) CN,
20) NR10R11, 21) N(R10)(CO)NR4R11, and,
22) O(CO)R4, or two R5 attached to the same carbon form the substituent =O, such that C(R5)2 may be C=O,
where the number of R5 substituents that are not H, can range from zero to three;
R6 is independently selected from: H, C1-6 alkyl, (F)pC1-6 alkyl, C3-6 cycloalkyl, aryl, heteroaryl and benzyl, unsubstituted or substituted with
  a) (F)pC1-3 alkyl,
  b) halogen,
  c) OR4,
  d) O(CH2)sOR4,
  e) CO2R4,
  f) (CO)NR10R11,
  g) O(CO)NR10R11,
  h) N(R4)(CO)NR10R11,
  i) N(R10)(CO)R11,
  j) N(R10)(CO)OR11,
  k) SO2NR10R11,
  l) N(R10) SO2R11,
  m) S(O)mR10,
  n) CN,
  o) NR10R11,
  p) N(R10)(CO)NR4R11, and
  q) O(CO)R4;
G_J is selected from: N, C(R5), C=C(R5), N—C(R5)2, C=N, C(R5)-C(R5)2, C(R5)-N(R6), and N—N(R6);
Q-T is selected from: C(R5)2-C(R5)2, C(R5)=C(R5), N=C(R5), C(R5)=N,N=N,N(R6), C(R5)2-(C=O), N(R6)-(C=O), and C(R5)2-N(R6);
R3 is independently selected from H, substituted or unsubstituted C1-C3 alkyl, CN, F, OR4 and CO2R4;
p is 0 to 2q+1, for a substituent with q carbons; m is 0, 1 or 2; s is 1, 2 or 3;

and pharmaceutically acceptable salts and individual diastereomers thereof.

Further embodiments of the invention are CGRP antagonists of Formula I which include compounds of the Formula Ia:

Ia wherein:
G-J and Q-T are as defined in Formula I;

and pharmaceutically acceptable salts and individual stereoisomers thereof.

Still further embodiments of the invention are CGRP antagonists of Formula I which include compounds of the Formula Ib:

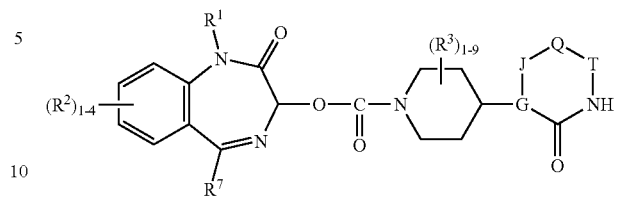

Ib wherein:
R5 and R6 are as defined in Formula I;

and pharmaceutically acceptable salts and individual stereoisomers thereof.

Further embodiments of the invention are CGRP antagonists of Formula I, wherein:
R1 is selected from:
  1) H, C1-C6 alkyl, C2-C6 alkenyl, C2-C6 alkynyl, C3-6 cycloalkyl, and heterocycle, unsubstituted or substituted with one or more substituents independently selected from:
    a) C1-6 alkyl,
    b) C3-6 cycloalkyl,
    c) aryl, unsubstituted or substituted with 1-5 substituents where the substituents are independently selected from R4,
    d) heteroaryl, unsubstituted or substituted with 1-5 substituents independently selected from R4,
    e) heterocycle, unsubstituted or substituted with 1-5 substituents independently selected from R4,
    f) (F)pC1-3 alkyl,
    g) halogen,
    h) OR4,
    i) O(CH2)s OR4,
    j) CO2R4,
    k) (CO)NR10R11,
    l) O(CO)NR10R11,
    m) N(R4)(CO)NR10R11,
    n) N(R10)(CO)R11,
    o) N(R10)(CO)OR11,
    p) SO2NR10R11,
    q) N(R10) SO2R11,
    r) S(O)mR10,
    s) CN,
    t) NR10R11,
    u) N(R10)(CO)NR4R11, and
    v) O(CO)R4; and
  2) aryl or heteroaryl, unsubstituted or substituted with one or more substituents independently selected from:
    a) C1-6 alkyl,
    b) C3-6 cycloalkyl,
    c) aryl, unsubstituted or substituted with 1-5 substituents independently selected from R4,
    d) heteroaryl, unsubstituted or substituted with 1-5 substituents independently selected from R4,
    e) heterocycle, unsubstituted or substituted with 1-5 substituents independently selected from R4,
    f) (F)pC1-3 alkyl,
    g) halogen,
    h) OR4,
    i) O(CH2)sOR4,
    j) CO2R4,
    k) (CO)NR10R11, l) O(CO)NR10R11,
m) N(R4)(CO)NR10R11,
n) N(R10)(CO)R11,
o) N(R10)(CO)OR11,
p) SO2NR10R11,
q) N(R10) SO2R11,
r) S(O)mR10,
s) CN,
t) NR10R11,
u) N(R10)(CO)NR4R11, and
v) O(CO)R4; and R2 is independently selected from H and:
1) C1-6 alkyl,
2) C3-6 cycloalkyl,
3) aryl, unsubstituted or substituted with 1-5 substituents independently selected from R4,
4) heteroaryl, unsubstituted or substituted with 1-5 substituents independently selected from R4,
5) heterocycle, unsubstituted or substituted with 1-5 substituents independently selected from R4,
6) (F)pC1-3 alkyl,
7) halogen,
8) OR4,
9) O(CH2)sOR4,
10) CO2R4,
11) (CO)NR10R11,
12) O(CO)NR10R11,
13) N(R4)(CO)NR10R11,
14) N(R10)(CO)R11,
15) N(R10)(CO)OR11,
16) SO2NR10R11,
17) N(R10)SO2R11,
18) S(O)mR10,
19) CN,
20) NR10R11,
21) N(R10)(CO)NR4R11, and
22) O(CO)R4;

R7 is selected from:
1) H, C0-C6 alkyl, C2-C6 alkenyl, C2-C6 alkynyl, C3-6 cycloalkyl and heterocycle, unsubstituted or substituted with one or more substituents independently selected from:
    a) C1-6 alkyl,
    b) C3-6 cycloalkyl,
    c) aryl, unsubstituted or substituted with 1-5 substituents where the substituents are independently selected from R4,
    d) heteroaryl, unsubstituted or substituted with 1-5 substituents independently selected from R4,
    e) heterocycle, unsubstituted or substituted with 1-5 substituents independently selected from R4,
    f) (F)pC1-3 alkyl,
    g) halogen,
    h) OR4,
    i) O(CH2)sOR4,
    j) CO2R4,
    k) (CO)NR10R11,
    l) O(CO)NR10R11,
    m) N(R4)(CO)NR10R11,
    n) N(R10)(CO)R11,
    o) N(R10)(CO)OR11,
    p) SO2NR10R11,
    q) N(R10) SO2R11,
    r) S(O)mR10,
    s) CN,
    t) NR10R11,
    u) N(R10)(CO)NR4R11,
    v) O(CO)R4; and
2) aryl or heteroaryl, unsubstituted or substituted with one or more substituents independently selected from:
    a) C1-6 alkyl,
    b) C3-6 cycloalkyl,
    c) aryl, unsubstituted or substituted with 1-5 substituents independently selected from R4,
    d) heteroaryl, unsubstituted or substituted with 1-5 substituents independently selected from R4,
    e) heterocycle, unsubstituted or substituted with 1-5 substituents independently selected from R4,
    f) (F)pC1-3 alkyl,
    g) halogen,
    h) OR4,
    i) O(CH2)sOR4,
    j) CO2R4,
    k) (CO)NR10R11,
    l) O(CO)NR10R11,
    m) N(R4)(CO)NR10R11,
    n) N(R10)(CO)R11,
    o) N(R10)(CO)OR11,
    p) SO2NR10R11,
    q) N(R10) SO2R11,
    r) S(O)mR10,
    s) CN,
    t) NR10R11,
    u) N(R10)(CO)NR4R11, and
    v) O(CO)R4;

R10 and R11 are independently selected from: H, C1-6 alkyl, (F)pC1-6 alkyl, C3-6 cycloalkyl, aryl, heteroaryl and benzyl, unsubstituted or substituted with halogen, hydroxy or C1-C6 alkoxy, where R10 and R11 may be joined together to form a ring selected from: azetidinyl, pyrrolidinyl, piperidinyl, piperazinyl and morpholinyl, which is unsubstituted or substituted with 1-5 substituents independently selected from R4

R4 is independently selected from: H, C1-6 alkyl, (F)pC1-6 alkyl, C3-6 cycloalkyl, aryl, heteroaryl and benzyl, unsubstituted or substituted with halogen, hydroxy or C1-C6 alkoxy;

W is O, NR4 or C(R4)2;

G_J is selected from:

N, such that when G-J is so defined, and Q-T is C(R5)2-C(R5)2 the following structure forms:

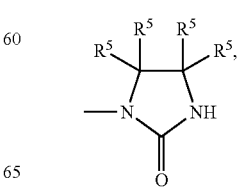

N, such that when G-J is so defined, and Q-T is C(R5)=C(R5) the following structure forms:

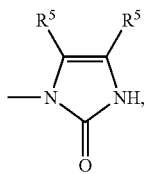

N, such that when G-J is so defined, and Q-T is N=C(R5) the following structure forms:

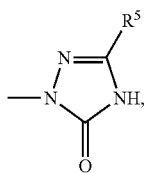

N, such that when G-J is so defined, and Q-T is C(R5)=N the following structure forms:

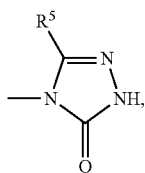

N, such that when G-J is so defined, and Q-T is N=N the following structure forms:

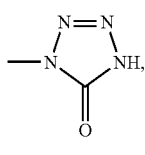

C=C(R5), such that when G-J is so defined, and Q-T is N(R6) the following structure forms:

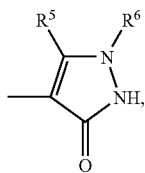

N, such that when G-J is so defined and Q-T is C(R5)2-(C=O) the following structure forms:

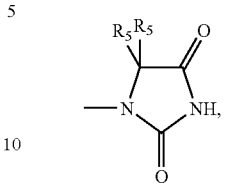

N—C(R5)2, such that when G-J is so defined and Q-T is C(R5)2-C(R5)2 the following structure forms:

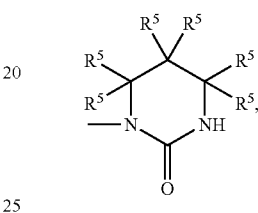

C=C(R5), such that when G-J is so defined and Q-T is C(R5)=C(R5) the following structure forms:

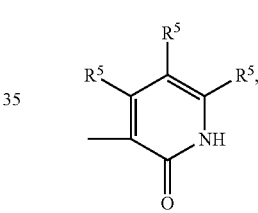

C=C(R5), such that when G-J is so defined and Q-T is C(R5)=N the following structure forms:

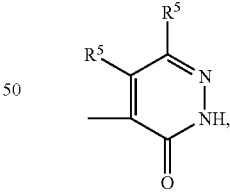

C=C(R5) such that when G-J is so defined and Q-T is N=C(R5) the following structure forms:

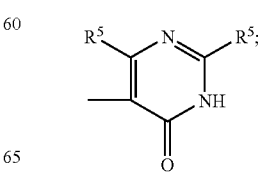

C=N, such that when G-J is so defined and Q-T is C(R5)=C(R5) the following structure forms:

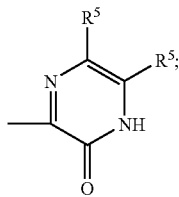

N—C(R5)2, such that when G-J is so defined and Q-T is C(R5)2-(C=O) the following structure forms:

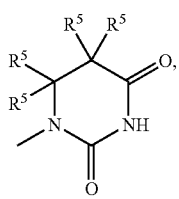

C(R5)-C(R5)2, such that when G-J is so defined and Q-T is N(R6)-(C=O) the following structure forms:

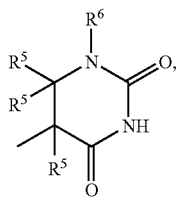

C(R5)-C(R5)2, such that when G-J is so defined and Q-T is C(R5)2-C(R5)2 the following structure forms:

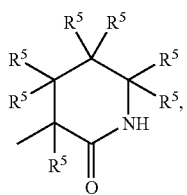

C(R5)-C(R5)2, such that when G-J is so defined and Q-T is C(R5)2-N(R6) the following structure forms:

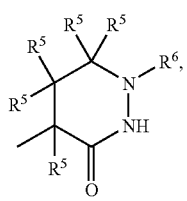

C(R5)-N(R6), such that when G-J is so defined and Q-T is C(R5)2-C(R5)2 the following structure forms:

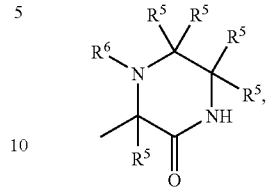

C(R5)-C(R5)2, such that when G-J is so defined and Q-T is N=C(R5) the following structure forms:

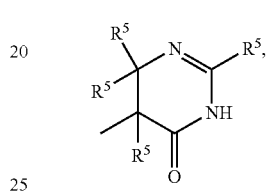

N—C(R5)2, such that when G-J is so defined and Q-T is C(R5)2-N(R6) the following structure forms:

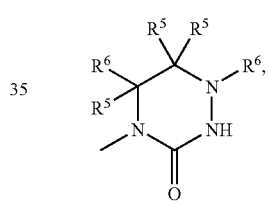

N-N(R6), such that when G-J is so defined and Q-T is C(R5)2-C(R5)2 the following structure forms:

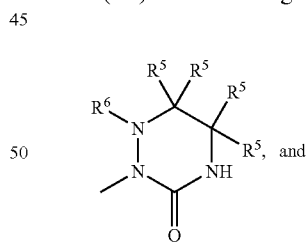

N—C(R5)2, such that when G-J is so defined and Q-T is N=C(R5) the following structure forms:

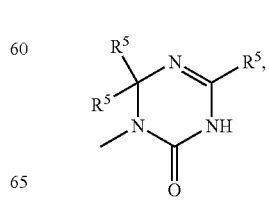

and tautomers;

R5 is independently selected from H and:
1) C1-C6 alkyl, C2-C6 alkenyl, C2-C6 alkynyl, C3-6 cycloalkyl and heterocycle, unsubstituted or substituted with one or more substituents independently selected from:
   a) C1-6 alkyl,
   b) C3-6 cycloalkyl.
   c) aryl, unsubstituted or substituted with 1-5 substituents independently selected from R4,
   d) heteroaryl, unsubstituted or substituted with 1-5 substituents independently selected from R4,
   e) heterocycle, unsubstituted or substituted with 1-5 substituents independently selected from R4,
   f) (F)pC1-3 alkyl,
   g) halogen,
   h) OR4,
   i) O(CH2)sOR4,
   j) CO2R4,
   k) (CO)NR10R11,
   l) O(CO)NR10R11,
   m) N(R4)(CO)NR10R11,
   n) N(R10)(CO)R11,
   o) N(R10)(CO)OR11,
   p) SO2NR10R11,
   q) N(R10) SO2R11,
   r) S(O)mR10,
   s) CN,
   t) NR10R11,
   u) N(R10)(CO)NR4R11, and,
   v) O(CO)R4;
2) aryl or heteroaryl, unsubstituted or substituted with one or more substituents independently selected from:
   a) C1-6 alkyl,
   b) C3-6 cycloalkyl,
   c) aryl, unsubstituted or substituted with 1-5 substituents where the substituents are independently selected from R4,
   d) heteroaryl, unsubstituted or substituted with 1-5 substituents independently selected from R4,
   e) heterocycle, unsubstituted or substituted with 1-5 substituents independently selected from R4,
   f) (F)pC1-3 alkyl,
   g) halogen,
   h) OR4,
   i) O(CH-2)sOR4,
   j) CO2R4,
   k) (CO)NR10R11,
   l) O(CO)NR10R11,
   m) N(R4)(CO)NR10R11,
   n) N(R10)(CO)R11,
   o) N(R10)(CO)OR11,
   p) SO2NR10R11,
   q) N(R10) SO2R11,
   r) S(O)mR10,
   s) CN,
   t) NR10R11,
   u) N(R10)(CO)NR4R11, and
   v) O(CO)R4;
3) C1-6 alkyl,
4) C3-6 cycloalkyl,
5) aryl, unsubstituted or substituted with 1-5 substituents independently selected from R4,
6) heteroaryl, unsubstituted or substituted with 1-5 substituents independently selected from R4,
7) heterocycle, unsubstituted or substituted with 1-5 substituents independently selected from R4,
8) (F)pC1-3 alkyl,
9) halogen,
10) OR4,
11) O(CH2)sOR4,
12) CO2R4,
13) (CO)NR10R11,
14) O(CO)NR10R11,
15) N(R4)(CO)NR10R11,
16) N(R10)(CO)R11,
17) N(R10)(CO)OR11,
18) SO2NR10R11,
19) N(R10) SO2R11,
20) S(O)mR10,
21) CN,
22) NR10R11,
23) N(R10)(CO)NR4R11, and
24) O(CO)R4, or two R5 attached to the same carbon form the substituent =O, such that C(R5)2 may be C=O, where the number of R5 substituents that are not H, can range from zero to three;

R3 is independently selected from H, substituted or unsubstituted C1-C3 alkyl, CN and CO2R4;

p is 0 to 2q+1, for a substituent with q carbons; m is 0 to 2; s is 1 to 3;

and pharmaceutically acceptable salts and individual stereoisomers thereof.

It is to be understood that where one or more of the above recited structures or substructures recite multiple substituents having the same designation each such variable may be the same or different from each similarly designated variable. For example, R2 is recited four times in formula I, and each R2 in formula I may independently be any of the substructures defined under R2. The invention is not limited to structures and substructures wherein each R2 must be the same for a given structure. The same is true with respect to any variable appearing multiple time in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the R10 and R11 substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus C1-6alkyl is defined to identify the group as having 1, 2, 3, 4, 5 or 6 carbons in a linear or branched arrangement, such that C1-6alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. C0 or C0alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. C2-6alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus C2-6alkynyl is defined to identify the group as having 2, 3, 4, 5 or 6 carbons in a linear or branched arrangement, such that C2-6alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, moipholine, morpholinone, oxazoline, oxazolidine, oxazolidinone, oxetane, 2-oxohexahydroazepin, 2-oxopiperazine, 2-oxopiperidine, 2-oxopyirolidinie, piperazine, piperidine, pyran, pyrazolidine, pyrazoline, pyrrolidine, pyrolione, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in C1-C6 alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "(F)pC1-3 alkyl" this means that when there is one carbon, there are 2(1)+1=3 fluorines. When there are two carbons, there are 2(2)+1=5 fluorines, and when there are three carbons there are 2(3)=1=7 fluorines.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of 125I-CGRP to receptors and functional antagonism of CGRP receptors were determined as follows:

NATIVE RECEPTOR BINDING ASSAY: The binding of 125I-CGRP to receptors in SK-N-MC cell membranes was carried out essentially as described (Edvinsson et al. (2001) Eur. J. Pharmacol. 415, 39-44). Briefly, membranes (25 g) were incubated in 1 ml of binding buffer [10 nM HEPES, pH 7.4, 5 mM MgCl2 and 0.2% bovine serum albumin (BSA)] containing 10 µM 125I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 1) was added and the radioactivity was counted on a Topcount (Packard Instrument). Data analysis was carried out by using Prism and the Ki was determined by using the Cheng-Prusoff equation (Cheng & Prusoff (1973) Biochem. Pharmacol. 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 g/ml streptomycin at 37° C., 95% humidity, and 5% CO2. For cAMP assays, cells were plated at $5\times10^5$ cells/well in 96-well poly-D-lysine-coated plates (Becton-Dickinson) and cultured for 18 h before assay. Cells were washed with phosphate-buffered saline (PBS, Sigma) then pre-incubated with 300 M isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) Br. J. Pharmacol. 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 370 C and 95% humidity. Cells were subcultured by treatment with 0.25% trypsin with 0.1% EDTA in IBSS. Stable cell line generation was accomplished by co-transfecting 10 ug of DNA with 30 ug Lipofectamine 2000 (Invitrogen) in 75 cm2 flasks. CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM MgCl2, and 0.2% BSA) for 3 hours at room temperature containing 10 μM 125I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was calTied out with the apparent dissociation constant (Ki) determined by using a non-linear least squares fitting the bound CPMI data to the equation below:

$$Y_{obsd} = (Y_{max} - Y_{min})(\%I_{max} - \%I_{min}/100) + Y_{min} + (Y_{max} - Y_{min})(100 - \%I_{max}/100)1 + ([Drug]/K_i(1 + [Radiolabel]/K_d)nH$$

Where Y is observed CPM bound, Ymax is total bound counts, Y min is non specific bound counts, (Y max−Y min) is specific bound counts, % I max is the maximum percent inhibition, % I min is the minimum percent inhibition, radiolabel is the probe, and the Kd is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 370 C and 95% humidity in Cellgro Complete Serum-Free/Low-Protein medium (Mediatech, Inc.) with L-glutamine and 1 g/L BSA. Isobutyl-methylxanthine was added to the cells at a concentration of 300 M and incubated for 30 min at 370 C. Human-CGRP was added to the cells at a concentration of 0.3 nM and allowed to incubate at 370 C. for 5 min. After -CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and IC50 values determined from a 4-parameter logistic fit as defined by the equation y=((a−d)/(1+(x/c)b)+d, where y=response, x=dose, a=max response, d 5=min response, c=inflection point and b=slope.

In particular, the compounds of the following examples had activity as antagonists of the CGRP receptor in the aforementioned assays, generally with a Ki or IC50 value of less than about 50 M. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an an anti-migraine agent, such as ergotamine and dihydroergotamine, or other serotonin agonists, especially a 5-HT1B/1D agonist, for example sumatriptan, naratriptan, zolmitriptan, eletriptan, almotriptan, frovatriptan, donitriptan, and rizatriptan, a 5-HT1D agonist such as PNU-142633 and a 5-HT1F agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabuinetone, tenidap, etanercept, tolmetin, phenylbutazonle, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphinie or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5HT2 receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotoinin reuptake inhibitor, for example fluoxetine, paroxetiine, sertraline, duloxetine, escitalopram, or citalopram; anantidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergoclyptine, α-ergociyptine, β-ergociyptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlpiperazine, chloipromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartini, valsaitan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, bromplieniramine, carbinoxamine, chloilpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT1 agonist, especially a 5-HT1B/1D agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. II general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agent.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of the lactams and 4-heteroarylpiperidine intermediates may be conducted as described in Schemes 1-15.

Reaction Schemes

The preparation of final compounds proceeds through intermediates such as those of Formula II and Formula III, and the synthesis of each intermediate is described herein.

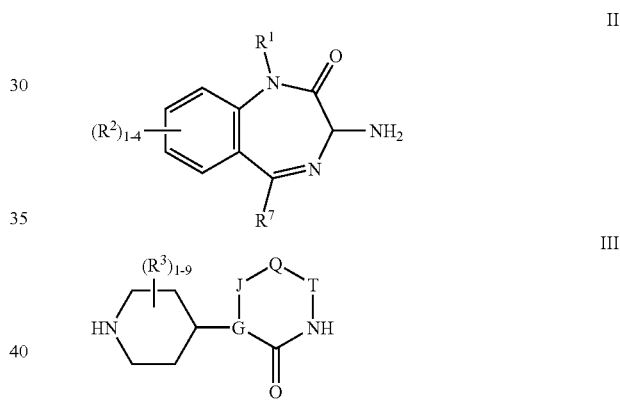

In general, intermediates of the Formulae II and III can be coupled through a urea linkage as shown in Scheme 1. Amine intermediate II can be converted to a reactive carbamate, for example p-nitrophenylcarbamate 1, which is subsequently reacted with an amine like that of intermediate 2 to produce urea 3. Other activated intermediates known to those skilled in the art can be used to prepare compounds like 3. For example, amine II can be directly acylated with the appropriate carbamoyl chloride.

SCHEME 1

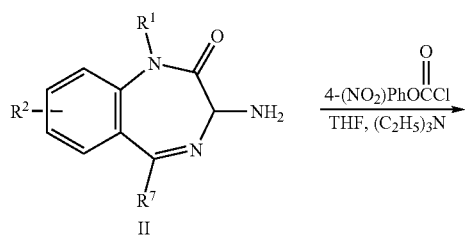

-continued

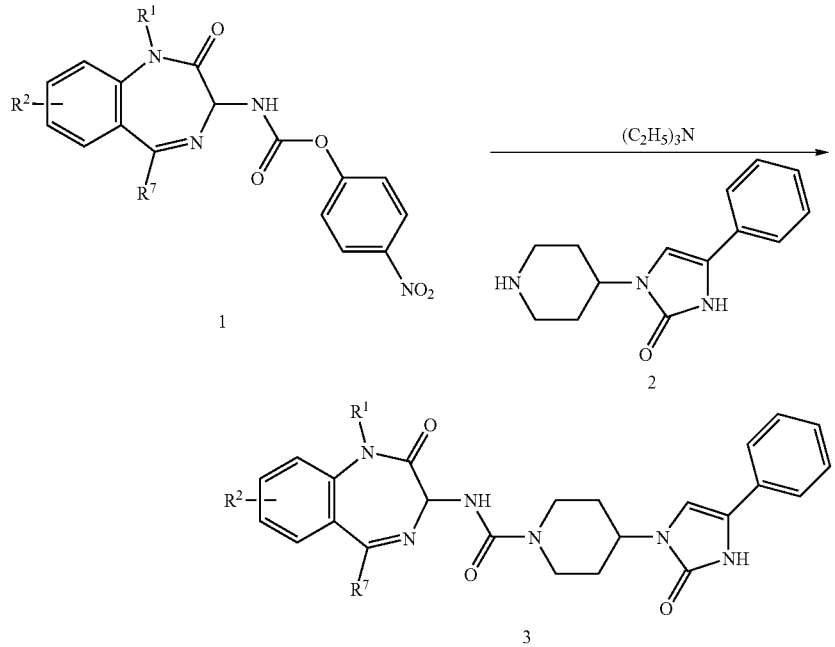

Representative syntheses for 3-amino-1,4-benzodiazepin-2-ones (e.g. II) include Bock et al., Tetrahedron Lett, 1987, 28, 939-942; Bock et al., J. Org. Chem., 1987, 52, 3232-3239; Sherrill et al., J. Org. Chem. 1995, 60, 730-734; Butcher et al, Tetrahedron Lett. 1996, 37, 6685-6688; and Selnick et al., J. Med. Chem. 1997, 40, 3865-3868. When the 3-amino group in Formula II is protected, for example with a carbonylbenzyloxy or t-butoxycarbonyl protecting group, the amide group ($R1=H$) can be selectively reacted with an alkylating agent using various bases and solvents, including sodium hydride or cesium carbonate in a polar aprotic solvent like dimethylformamide. Subsequent deprotection produces the requisite 3-amino-1,4-benzodiazepin-2-one intermediate II (Scheme 2).

SCHEME 2

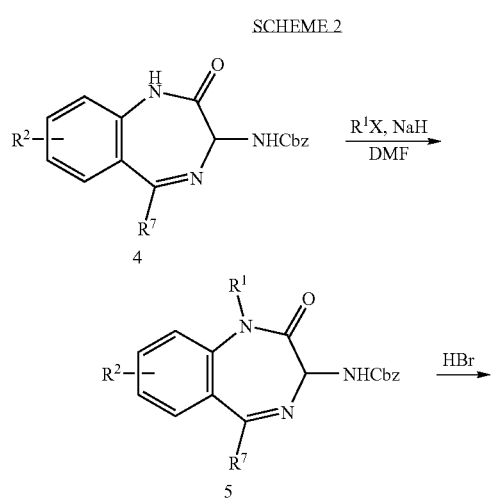

-continued

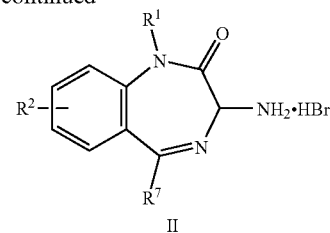

Chiral resolution of the amine intermediate can be accomplished by a number of methods, including those described by Rittle et al., Tetrahedron Lett., 1987, 28, 521-522; Reider, Chem. & Indus. 1988, 12, 394-398; Reider et al., J. Org. Chem. 1987, 52, 955-957; Sherrill et al., J. Org. Chem. 1995, 60, 730-734; Shi et al., Tetrahedron, 1999, 55, 909-918.

Using 3-hydroxybenzodiazepine 6 in place of 3-aminobenzodiazepine, the analogous carbamates can be prepared. Compounds like 6 are commercially available, or prepared by known procedures. One synthesis is illustrated in 3, where bromination and subsequent hydrolysis provides the requisite intermediate 3-hydroxybenzodiazepinone. The 3-hydroxybenzodiazepinone can be converted to carbamate 8 through reaction of the activated p-nitrophenylcarbonate with the appropriate amine.

SCHEME 3

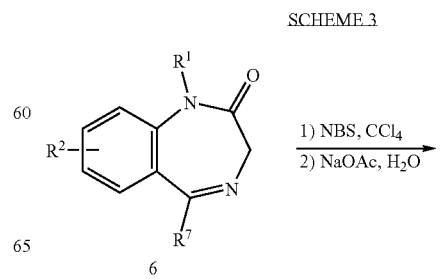

-continued

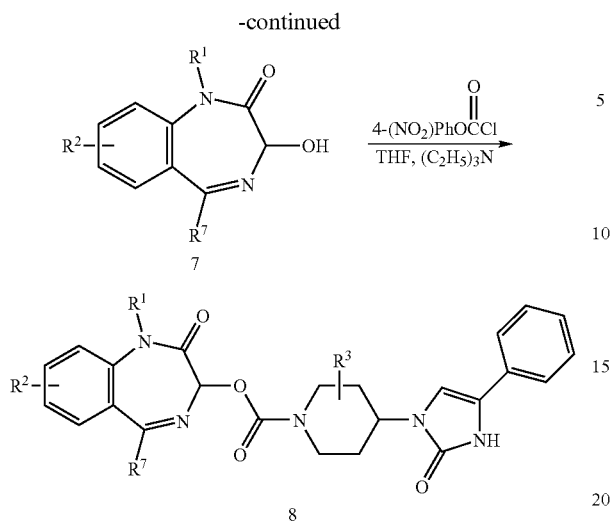

The synthesis of compounds represented by 3 can be accomplished by procedures similar to those described in U.S. Pat. No. 6,344,449 and references cited therein. Alternatively, these compounds can be prepared according to Scheme 4. Coupling of a protected 4-aminopiperidine 9 with an -amino ester gives an urea 11. Reduction and cyclodehydration (Synlett, 1997, p. 521) or reduction and oxidation/cyclization gives 12, which after standard deprotection yields the target compounds 13.

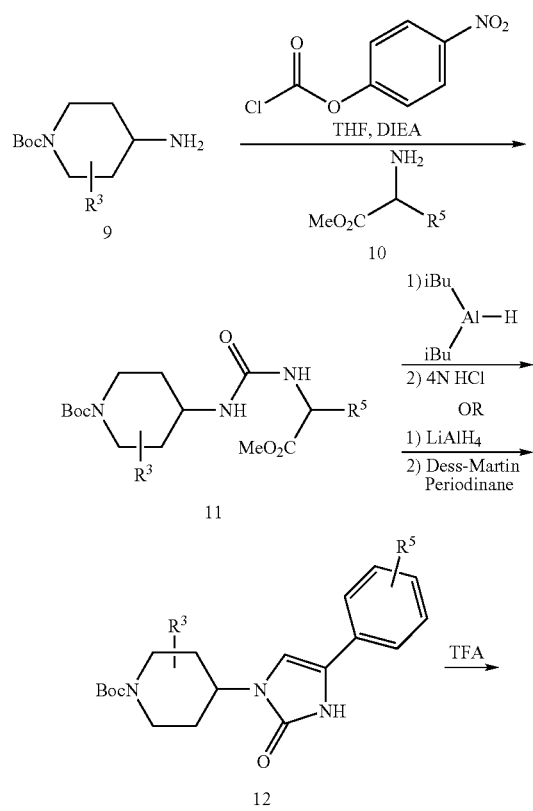

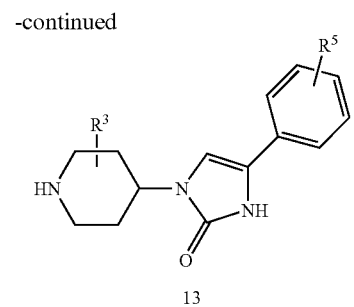

The double bond of 13 may be hydrogenated to give 14 (Scheme 5).

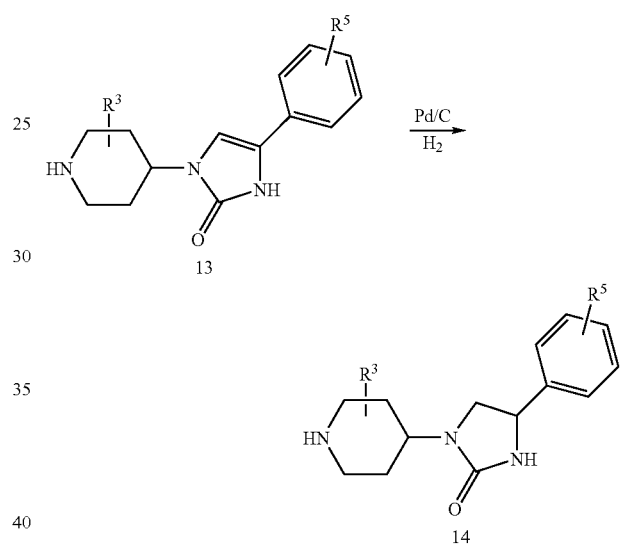

The synthesis of compounds represented by 21 can be accomplished according to Scheme 6. For example, a 4-piperidinone 15 can be reductively aminated with a carbazate which, after reduction of hydrazone 16, gives the monalkylated product 17. Deprotection to afford hydrazine 18 and condensation/ring closure with a benzothioyl carbamate such as 19 furnishes triazolinone 20. Final deprotection under standard conditions gives the product 21.

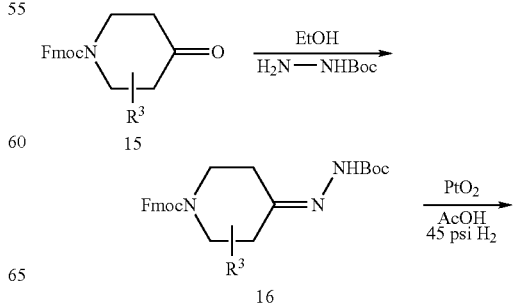

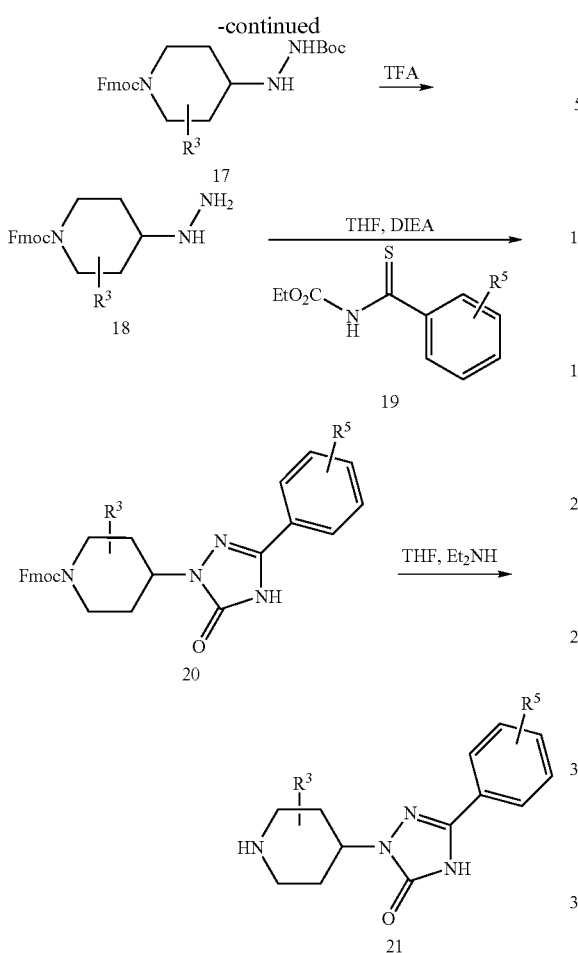

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products.

EXAMPLES

The following intermediates and examples are provided so that the invention might be more fully understood. These examples are illustrative only and should not be construed as limiting the invention in any way.

Intermediate 1

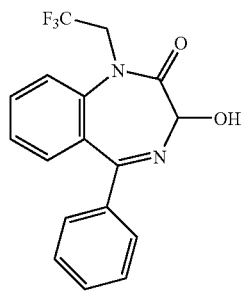

3-Hydroxy-2-oxo-5-phenyl-1-(2,2,2-trifluoroethyl)-2,3-dihydro-1H-1,4-benzodiazepine N-Bromosuccinimide (0.335 g, 1.88 mmol) was added to a solution of 2-oxo-5-phenyl-1-(2,2,2-trifluoroethyl)-2,3-dihydro-1H-1,4-benzodiazepine (H. G. Selnick et al., J. Med. Chem., 1997, 40, 3865-3868) (0.500 g, 1.57 mmol) in carbon tetrachloride (20 mL) at room temperature. After 15 min, trifluoroacetic acid (1.0 mL) was added, and the reaction refluxed for 5 h. The reaction was cooled and concentrated. The residue was dissolved in 5% aqueous sodium acetate (15 mL) and acetone (10 mL) and stirred overnight. The reaction was concentrated and worked up, and the crude product purified by chromatography (silica gel, 0-30% ethyl acetate in hexane gradient elution), providing the title compound. MS 335 (M+1) 1H NMR (500 MHz, CDCl3) ☐ 7.92-7.30 (9H, m), 5.21 (dq, J=15, 8 Hz, 1H), 5.07 (d, J=10 Hz, 0.5H), 4.51 (d, J=10 Hz, 0.5H), 4.22 (t, dq, J=15, 8 Hz, 1H).

Intermediate 2

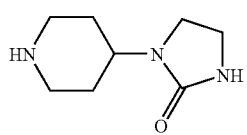

1-Piperidin-4-ylimidazolidin-2-one

Step A. 1-t-Butoxycarbonyl-4-(2-chloroethylamino)piperidine

A solution of 4-amino-1-t-butoxycarbonylpiperidine (200 mg, 1.0 mmol) in tetrahydrofuran (5 mL) was treated with 2-chloroethyl isocyanate (0.090 mL, 1.0 mmol) overnight. The solvent was evaporated to provide the title compound as a white solid (305 mg).

Step B. 1-(1-t-Butoxycarbonylpiperidin-4-yl)imidazolidin-2-one

Sodium hydride (59 mg, 60% dispersion in oil, 1.5 mmol) was added to a solution of 1-t-butoxycarbonyl-4-(2-chloroethylamino)piperidine (305 mg, 0.98 mmol) in dimethylformamide (5 mL), and the reaction stirred at room temperature overnight. The reaction was quenched with water, filtered and purified by reverse phase HPLC(C-18, 5% to 95% 0.1% trifluoroacetic acid/acetonitrile in 0.1% aqueous trifluoroacetic acid, gradient elution), to give the title compound (30 mg). $^1$H NMR (500 MHz, CDCl3) ☐ 4.22 (br s, 3H), 3.88 (tt, J=4, 12 Hz, 1H), 3.52 (m, 2H), 3.46 (m, 2H), 2.79 (br t, 11 Hz, 2H), 1.72 (d, J=12 Hz, 2H), 1.56 (m, 2H), 1.48 (s, 9H).

Step C. 1-(Piperidin-4-yl)imidazolidin-2-one

Trifluoroacetic acid (0.5 mL) was added to a solution of 1-(1-t-butoxycarbonylpiperidin-4-yl)imidazolidin-2-one (30 mg, 0.11 mmol) in dichloromethane (2 mL) and the reaction stirred at room temperature for 5 h. The reaction was concentrated in vacuo to give the title compound as its trifluoroacetic acid salt (18 mg).

Intermediate 3

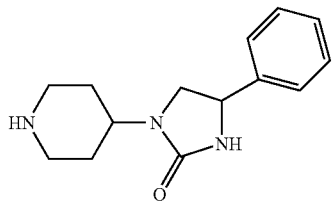

4-Phenyl-1-piperidin-4-yl-imidazolidin-2-one

A solution of 4-phenyl-1-piperidin-4-yl-1,3-dihydro-2H-imidazol-2-one hydrochloride (510 mg, 1.82 mmol) in methanol (10 mL) was hydrogenated at 1 atm hydrogen over palladium on carbon (100 mg). After 4 h, the reaction was filtered and the crude product purified by reverse phase HPLC (C-18, 5% to 95% 0.1% trifluoroacetic acid/acetonitrile in 0.1% aqueous trifluoroacetic acid gradient elution). The title compound was obtained as the trifluoroacetic acid salt (304 mg). MS 246 (M+1)

Intermediate 4

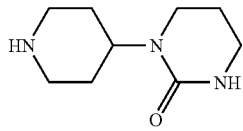

1-Piperidinyl-4-yltetrahydropyrimidin-2[1H]-one

Step A. 1-t-Butoxycarbonyl-4-(3-chloropropylamino)piperidine

A solution of 4-amino-1-t-butoxycarbonylpiperidine (200 mg, 1.0 mmol) in tetrahydrofuran (5 mL) was treated with 3-chloropropyl isocyanate (0.080 mL, 1.0 mmol) overnight. The solvent was evaporated to provide the title compound as a white solid (270 mg).

Step B. 1-(1-t-Butoxycarbonylpiperidinyl-4-yl)tetrahydropyrimidin-2[1H]-one

Sodium hydride (19 mg, 60% dispersion in oil, 0.47 mmol) was added to a solution of 1-t-butoxycarbonyl-4-(2-chloroethylamino)piperidine (100 mg, 0.31 mmol) in dimethylformamide (5 mL), and the reaction stirred at room temperature overnight. The reaction was quenched with water, and extracted with ethyl acetate. The organic phase was washed with saturated brine and dried over magnesium sulfate. The title compound was obtained as a white solid (20 mg).

Step C.
1-Piperidin-4-yltetrahydropyrimidin-2-[1H]-one

Trifluoroacetic acid (0.5 mL) was added to a solution of 1-(1-t-butoxycarbonylpiperidin-4-yl)imidazolidin-2-one (20 mg, 0.07 mmol) in dichloromethane (2 mL) and the reaction stirred at room temperature overnight. The reaction was concentrated in vacuo to give the title compound as its trifluoroacetic acid salt (12 mg).

Intermediate 5

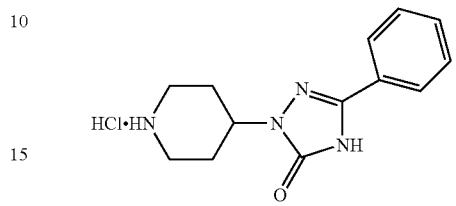

5-Phenyl-1-piperidin-4-yl-2,4-dihydro-3H-1,2,4-triazol-3-one hydrochloride

Step A. 9H-Fluoren-9-ylmethyl 4-[(t-butoxycarbonyl)hydrazono]piperidine-1-carboxylate A solution of 1-[(9H-fluoren-9-yl)methyloxycarbonyl]-4-piperidone (16.0 g. 50.0 mmol) and t-butyl carbazate 7.25 g, 55.5 mmol) in ethanol (250 mL) was refluxed for 1 h. The solution was cooled and concentrated. Addition of ether (100 mL) produced the title compound as a white precipitate (21.0 g). $^1$H NMR (500 MHz, CDCl3) ☐ 7.77 (d, J=7 Hz, 2H), 7.57 (d, J=7 Hz, 2H), 7.40 (t, J=7 Hz, 2H), 7.32 (t, J=7 Hz, 2H), 4.50 (br s, 2H), 4.24 (t, J=6 Hz, 1H), 3.4-3.7 (br m, 4H), 2.47 (br s, 2H), 2.1-2.2 (br m, 2H), 1.56 (s, 9H).

Step B. 9H-Fluoren-9-ylmethyl 4-[(t-butoxycarbonyl)hydrazino]piperidine-1-carboxylate A solution of 9H-fluoren-9-ylmethyl 4-[(t-butoxycarbonyl)hydrazono]piperidine-1-carboxylate (10.0 g, 22.9 mmol) in acetic acid (150 mL) was shaken with platinum oxide (1.0 g) under 45 psi hydrogen on a Parr apparatus for 2 h. The solution was filtered and concentrated to give the title compound.

Step C. 9H-Fluoren-9-ylmethyl 4-hydrazinopiperidine-1-carboxylate

A solution of 9H-fluoren-9-ylmethyl 4-[(t-butoxycarbonyl)hydrazino]piperidine-1-carboxylate (20 g, 45.7 mmol) was dissolved in trifluoroacetic acid (100 mL) and stirred at room temperature for 1.5 h. The reaction was concentrated and the residue dissolved in methanol and purified by reverse phase HPLC. Pure fractions were isolated and combined to give the trifluoroacetic acid salt of the title compound (3.01 g). $^1$H NMR (500 MHz, DMSO-d6) ☐ 7.89 (d, J=8 Hz, 2H), 7.61 (d, J=8 Hz, 2H), 7.40 (t, J=8 Hz, 2H), 7.32 (t, J=8 Hz, 2H), 4.33 (d, J=6 Hz, 2H), 4.25 (t, J=6 Hz, 1H), 3.5-4.0 (br s, 6H), 3.05 (br s, 1H), 2.80 (br 2, 2H), 1.89 (br s, 2H), 1.2 (br s, 2H).

Step D. 9H-Fluoren-9-ylmethyl 4-(5-oxo-3-phenyl-4,5-dihydro-1H-1,2,4-triazol-1-yl)piperidine-1-carboxylate A solution of 9H-fluoren-9-ylmethyl 4-hydrazinopiperidine-1-carboxylate trifluoroacetic acid salt (2.95 g, 6.54 mmol) was refluxed for 2 h with ethyl N-benzothioyl carbamate (1.50 g, 7.1 mmol) (prepared by the procedure of E. P. Papadopoulus, J. Org. Chem., 1976, 41(6) 962-965) in tetrahydrofuran (30 mL) with diisopropylethyl amine (1.25 mL, 7.1 mmol). The reaction was cooled and concentrated, then dissolved with heating in acetonitrile. A white solid crystallized upon cooling, giving the title compound (2.06 g). $^1$H NMR (500 MHz, CDCl3) ☐ 7.80 (d, J=7 Hz, 2H), 7.77 (d, J=7 Hz, 2H), 7.61 (d, J=7 Hz, 2H), 7.48 (m, 3H), 7.40 (t, J=7 Hz, 2H), 7.33 (t, J=7 Hz, 2H), 4.46 (d, J=6 Hz, 2H), 4.36 (m, 2H), 4.27 (t, J=6 Hz, 1H), 4.26 (br s, 1H), 3.02 (br s, 2H), 2.04 (br s, 2H), 1.94 (br m, 2H).

Step F. 5-Phenyl-1-piperidin-4-yl-2,4-dihydro-3H-1,2,4-triazol-3-one hydrochloride A solution of 9H-fluoren-9-ylmethyl 4-(5-oxo-3-phenyl-4,5-dihydro-1H-1,2,4-triazol-1-yl)piperidine-1-carboxylate (2.06 g, 4.41 mmol) and diethylamine (15 mL) in tetrahydrofuran (15 mL) was stirred at room temperature for 2 h. The reaction was concentrated and the crude product purified by column chromatography (silica gel, 0 to 10% {5% ammonium hydroxide/methanol} in methylene chloride gradient elution), giving the title compound as a white solid (0.95 g). $^1$H NMR (500 MHz, CDCl3) ☐ 7.84 (d, J=7 Hz, 2H), 7.47 (m, 3H), 4.30 (m, 1H), 3.25 (d, J=13 Hz, 2H), 2.79 (t, J=13 Hz, 2H), 2.04 (dq, J=4, 12 Hz, 2H), 1.93 (br d, J=10 Hz, 2H).

Intermediate 6

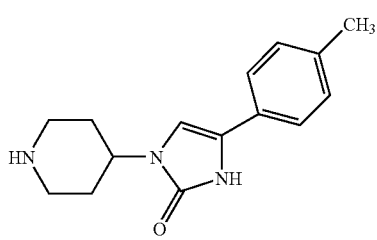

4-(4-Methylphenyl)-1-piperidin-4-yl-1,3-dihydro-2H-imidazol-2-one

Step A. tert-Butyl 4-[4-(4-methylphenyl)-2-oxo-2,3-dihydro-1H-imidazol-1-yl]piperidine-1-carboxylate Sodium acetate (41 mg, 0.50 mmol) was added to a solution of t-butyl 4-aminopiperidine-1-carboxylate (100 mg, 0.50 mmol) in acetonitrile (2 mL) at 0° C. After 5 min, 2-bromo-4'-methylacetophenone (106.4 mg, 0.50 mmol) in acetonitrile (1 mL) was added and the mixture was allowed to warm to ambient temperature. After 1.5 h, sodium cyanate (97.4 mg, 1.5 mmol), acetic acid (100 uL) and water (80 uL) were added to the reaction mixture. After 16 h, the mixture was concentrated to give the title compound.

Step B. 4-(4-Methylphenyl)-1-piperidin-4-yl-1,3-dihydro-2H-imidazol-2-one

Trifluoroacetic acid (0.600 mL) was added to a solution tert-butyl 4-[4-(4-methylphenyl)-2-oxo-2,3-dihydro-1H-imidazol-1-yl]piperidine-1-carboxylate (178.4 mg, 0.50 mmol) in dichloromethane (3 mL). After 16 h, the reaction was concentrated and purified by reverse phase HPLC (C-18 column, 95% water/acetonitrile→5% water/acetonitrile with 0.1% trifluoroacetic acid) to give the title product. MS 258.1 (M+1).

Essentially following the procedures outlined for the foregoing Intermediate, the compounds listed in Table 1 were prepared.

TABLE 1

| Int. | R | MS (M + 1) |
|---|---|---|
| 7L-238 634 | 4-OCH3 | 274.1 |
| 8L-251 624 | 4-OCF3 | 328.1 |
| 9 | 4-OCHF2 | 310.1 |
| 10 | 3-OCH3 | 274.1 |
| 11 | 3-F | 262.0 |

Intermediate 7 and 7a

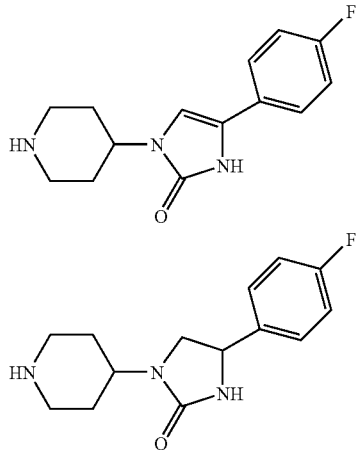

4-(4-Fluorophenyl)-1-piperidin-4-yl-1,3-dihydro-2H-imidazol-2-one and 4-(4-fluorophenyl)-1-piperidin-4-ylimidazolidin-2-one Step A. Methyl amino(4-fluorophenyl)acetate HCl (g) was bubbled into a solution of 4-fluoro-DL-phenylglycine (810 mg, 4.79 mmol) in methanol (20 mL) for 5 min at 0° C. The reaction warmed to ambient temperature and stirred for 18 h. The mixture was concentrated to give the title compound (1 g). MS 183.9 (M+1)

Step B. Methyl ({[(1-benzylpiperidin-4-yl)amino]carbonyl}amino)(4-fluorophenyl)acetate 4-Amino-1-benzylpiperidine (460 mg, 2.42 mmol) in tetrahydrofuran (15 mL) was added to a solution of p-nitrophenylchloroformate (487 mg, 2.42 mmol) and diisopropylethylamine (430 uL, 2.42 mmol) in tetrahydrofuran (5 mL) at 0° C. After 1 h, additional diisopropylethylamine was added (860 uL, 4.84 mmol) along with methyl amino(4-fluorophenyl)acetate (443 mg, 2.42 mmol). The reaction was warmed to room temperature and stirred overnight. The mixture was filtered, concentrated and redissolved in ethyl acetate. The ethyl acetate layer was washed with 1N sodium hydroxide (3×), saturated sodium bicarbonate solution, water, brine, and dried over sodium sulfate. The crude product was purified by column chromatography (silica gel, 0 to 5%/methanol in methylene chloride gradient elution), giving the title compound (700 mg). MS 400.29 (M+1)

Step C. 1-(1-Benzylpiperidin-4-yl)-4-(4-fluorophenyl)-1,3-dihydro-2H-imidazol-2-one Diisobutylaluminum hydride (1 M, 1.18 mL, 1.18 mmol) was added to a solution of methyl ({[(1-benzylpiperidin-4-yl)amino]carbonyl}amino)(4-fluorophenyl)acetate (430 mg, 1.08 mmol) in toluene (5 mL) and dichloromethane (5 mL) at −78° C. and stirred for 30 min and then warmed to 0° C. After 20 min at 0° C., the reaction was quenched with 1 N saturated potassium sodium tartrate solution (20 mL) and the mixture was extracted with ethyl acetate (2×). The combined organic extracts were dried over sodium sulfate, filtered, and concentrated. The crude material was treated with 4 N HCl in dioxane (4 mL), and stirred for 5 min. The mixture was concentrated, dissolved in dichloromethane and extracted with saturated sodium bicarbonate (2×). The combined organic extracts were dried over sodium sulfate, filtered, and concentrated. Purification by column chromatography (silica gel, 0 to 7% {1% ammonium hydroxide/methanol} in methylene chloride gradient elution), gave the title compound (150 mg). MS 400.29 (M+1)

Step D. 4-(4-Fluorophenyl)-1-piperidin-4-yl-1,3-dihydro-2H-imidazol-2-one and 4-(4-fluorophenyl)-1-piperidin-4-ylimidazolidin-2-one 10% Palladium on carbon (50 mg) was added to a solution of 1-(1-benzylpiperidin-4-yl)-4-(4-fluorophenyl)-1,3-dihydro-2H-imidazol-2-one (75 mg, 0.213 mmol) in ethanol (7.5 mL) and methanol (7.5 μL). The reaction vessel was evacuated and back-filled with nitrogen (3×), then back-filled with hydrogen (1 atm). After 5 h, the mixture was filtered and concentrated to give the title compounds in a 9:1 mixture (unsaturated: saturated). MS 262.27 and 264.31 (M+1)

Intermediate 8

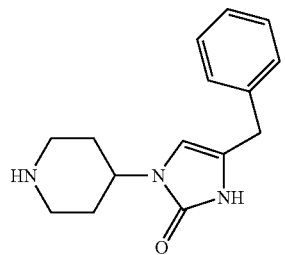

4-Benzyl-1-piperidin-4-yl-1,3-dihydro-2H-imidazol-2-one

Step A. Methyl N-{[(1-benzylpiperidin-4-yl)amino]carbonyl} phenylalaninate

DL-Phenylalanine methyl ester hydrochloride (1.3 g, 7.2 mmol) and triethylamine (2.2 mL, 15.8 mmol) in dichloromethane (100 mL) were added to a solution of p-nitrophenylchloroformate (1.45 g, 7.2 mmol) in dichloromethane (100 mL) at 0° C. After 1 h, the reaction was concentrated, redissolved in dioxane (50 mL) and 4-amino-1-benzylpiperidine (1.64 g, 8.6 mmol) and diisopropylethylamine (2.5 mL, 14.35 mmol) were added to the mixture. After 2 h, the mixture was concentrated and partitioned between dichloromethane and saturated sodium bicarbonate. The organic layer was dried over sodium sulfate, filtered, and concentrated. Purification by silica gel chromatography (1% ethyl acetate/hexanes→60% ethyl acetate/hexanes) gave the title compound (800 mg). MS 396.3 (M+1).

Step B. 4-Benzyl-1-(1-benzylpiperidin-4-yl)-1,3-dihydro-2H-imidazol-2-one

Diisobutylaluminum hydride (1M, 2.53 mL, 2.53 mmol) was added to a solution of methyl N-{[(1-benzylpiperidin-4-yl)amino]carbonyl}phenylalaninate (800 mg, 2.02 mmol) in toluene (7.5 mL) and dichloromethane (7.5 μL) at −78° C. and stirred for 30 min and then warmed to ambient temperature. After 5 min at room temperature, the reaction was quenched with saturated potassium sodium tartrate solution (20% solution), extracted with dichloromethane and treated with a 4 N HCl solution (50 mL). After 30 min. the mixture was extracted with water, basified to pH=7, and extracted with dichloromethane (3×). The combined organic extracts were dried over sodium sulfate, filtered, and concentrated. Purification by column chromatography (silica gel, 0 to 8% {1% ammonium hydroxide/methanol} in methylene chloride gradient elution), gave the title compound (250 mg). MS 348.3 (M+1)

Step C. 4-Benzyl-1-piperidin-4-yl-1,3-dihydro-2H-imidazol-2-one

10% Palladium on carbon (50 mg) was added to a solution of 4-benzyl-1-(1-benzylpiperidin-4-yl)-1,3-dihydro-2H-imidazol-2-one (100 mg, 0.287 mmol) in methanol (7.5 mL) and acetic acid (7.5 mL). The reaction vessel was evacuated and back-filled with nitrogen (3×), then back-filled with hydrogen (1 atm). After 16 h, the mixture was filtered and concentrated to give the title compound. MS 258.1 (M+1)

Intermediate 9

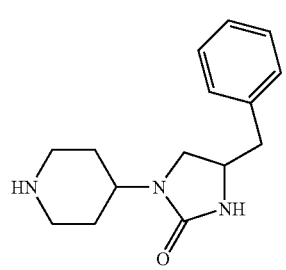

4-Benzyl-1-piperidin-4-ylimidazolidin-2-one

Step A. 5-Benzyl-3-(1-benzylpiperidin-4-yl)imidazolidine-2,4-dione

Sodium ethoxide (0.1301 mL, 1.66 mmol, 21% wt.) was added to a solution of methyl N-{[(1-benzylpiperidin-4-yl)amino]carbonyl}phenylalaninate (546 mg, 1.38 mmol) in ethanol (715 mL) at 0° C. and then warmed to ambient temperature. The reaction was concentrated and partitioned between ethyl acetate and water. The organic layer was washed with brine, dried over sodium sulfate, filtered, and concentrated to give the title compound (490 mg). MS 364.2 (M+1)

Step B. 4-Benzyl-1-(1-benzylpiperidin-4-yl)imidazolidin-2-one

Lithium aluminum hydride (3.96 mL, 3.96 mmol, 1 M) was added to a solution of 5-benzyl-3-(1-benzylpiperidin-4-yl)imidazolidine-2,4-dione (120 mg, 0.330 mmol) in tetrahydrofuran (15 mL) at 0° C. and then warmed to ambient temperature. After 16 h, the reaction was quenched with water (0.150 mL), a 15% sodium hydroxide solution (0.150 mL), and water (0.450 mL). The mixture was filtered, washed with tetrahydrofuran, and concentrated. Purification by column chromatography (silica gel, 1 to 12% {1% ammonium hydroxide/methanol} in methylene chloride gradient elution), gave the title compound (30 mg). MS 350.3 (M+1)

Step C. 4-Benzyl-1-piperidin-4-ylimidazolidin-2-one

10% palladium on carbon (10 mg) was added to a solution of 4-benzyl-1-(1-benzylpiperidin-4-yl)imidazolidin-2-one (30 mg, 0.086 mmol) in ethanol (15 mL) and concentrated hydrochloric acid (0.05 mL). The reaction vessel was evacuated and back-filled with nitrogen (3×), then back-filled with hydrogen (40 psi). After 16 h, the mixture was filtered and concentrated to give the title compound (20 mg). MS 260.3 (M+1)

Intermediate 10

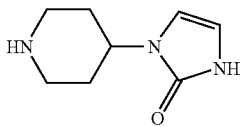

1-Piperidin-4-yl-1,3-dihydro-2H-imidazol-2-one

Step A. Methyl N-{[(1-(tert-butoxycarbonyl)piperidin-4-yl)amino]carbonyl}glycinate 4-Amino-1-boc-piperidine (964 mg, 4.8 mmol) in tetrahydrofuran (15 mL) was added to a solution of p-nitrophenylchloroformate (970 mg, 4.8 mmol) and triethylamine (0.67 mL, 4.8 mmol) in tetrahydrofuran (15 mL) at 0° C. After 1 h, additional diisopropylethylamine was added (1.3 mL, 9.6 mmol) along with glycine methyl ester hydrochloride (604 mg, 4.8 mmol). The reaction was warmed to room temperature and stirred overnight. The mixture was filtered, concentrated and redissolved in ethyl acetate. The ethyl acetate layer was washed with 1N sodium hydroxide (3×), saturated sodium bicarbonate solution, water, brine, and dried over sodium sulfate. Purification by silica gel chromatography (100% dichloromethane→8% methanol {1% ammonium hydroxide}/dichloromethane) gave the title compound (700 mg). MS 400.29 (M+1)

Step B. 1-Piperidin-4-yl-1,3-dihydro-2H-imidazol-2-one

Diisobutylaluminum hydride (1M, 0.875 µL, 0.875 mmol) was added to a solution of methyl N-{[(1-(tert-butoxycarbonyl)piperidin-4-yl)amino]carbonyl}glycinate (230 mg, 0.729 mmol) in toluene (5 µL) and dichloromethane (5 mL) at −78° C. and stirred for 30 min and then warmed to ambient temperature. After 30 min at room temperature, the reaction was quenched with 1 N saturated potassium sodium tartrate solution (15 mL) and extracted with dichloromethane (2×). The combined organic extracts were dried over sodium sulfate, filtered, concentrated. The crude material was dissolved in dichloromethane (10 µL) and treated with trifluoroacetic acid (5 mL). After 25 min, the reaction was concentrated to give the title compound. MS 168.3 (M+1)

Intermediate 11

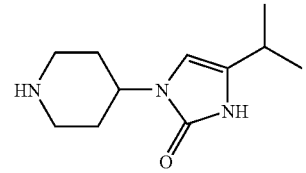

4-Isopropyl-1-piperidin-4-yl-1,3-dihydro-2H-imidazol-2-one

Step A. Methyl N-{[(1-tert-butoxycarbonylpiperidin-4-yl)amino]carbonyl}valinate

4-Amino-1-boc-piperidine (205 mg, 1.02 mmol) and triethylamine (0.143 µL, 1.02 mmol) in tetrahydrofuran (5 mL) were added to a solution of p-nitrophenylchloroformate (206 mg, 1.02 mmol) in tetrahydrofuran (15 mL) at 0° C. After 1 h, additional triethylamine was added (0.286 mL, 2.04 mmol) along with DL-valine methyl ester hydrochloride (134 mg, 1.02 mmol). The reaction warmed to ambient temperature and was then heated to 50° C. After 2 h, the mixture was filtered, concentrated and redissolved in ethyl acetate. The ethyl acetate layer was washed with 1N sodium hydroxide (3×), saturated sodium bicarbonate solution, water, brine, and dried over sodium sulfate. Purification by silica gel chromatography (100% dichloromethane→7% methanol {1% ammonium hydroxide}/dichloromethane) gave the title compound (300 mg). MS 358.28 (M+1)

Step B. 4-Isopropyl-1-piperidin-4-yl-1,3-dihydro-2H-imidazol-2-one

Diisobutylaluminum hydride (1M, 0.520 mL, 0.520 mmol) was added to a solution of methyl N-{[(1-tert-butoxycarbonylpiperidin-4-yl)amino]carbonyl}valinate (155 mg, 0.434 mmol) in toluene (3 mL) and dichloromethane (3 mL) at −78° C. and stirred for 30 min and then warmed to ambient temperature. After 1 h, the reaction was quenched with 1 N saturated potassium sodium tartrate solution (3 mL) and extracted with dichloromethane (2×). The combined organic extracts were dried over sodium sulfate, filtered, concentrated. The crude material was dissolved in dichloromethane (5 mL) and treated with trifluoroacetic acid (5 mL). After 30 min, the reaction was concentrated to give the title compound. MS 210.1 (M+1)

Intermediate 12

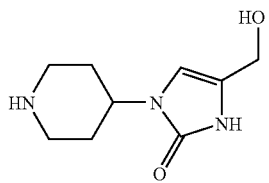

4-(Hydro-oxymethyl)-1-piperidin-4-yl-1,3-dihydro-2H-imidazol-2-one

Step A. Methyl O-[tert-butyl(diphenyl)silyl]serinate

Imidazole (2.82 g, 41.43 mmol) and tert-butyldiphenylchlorosilane (3.23 mL, 12.43 mmol) was added to a solution of DL-serine methyl ester hydrochloride (1.41 g, 11.84 mmol) in dimethylformamide (6 mL). After 16 h, the mixture was concentrated and partitioned between ethyl acetate and saturated sodium bicarbonate solution. The organic layer was dried over sodium sulfate, filtered, and concentrated. Purification by silica gel chromatography (100% dichloromethane=10% methanol {1% ammonium hydroxide}/dichloromethane) gave the title compound. MS 358.22 (M+1)

Step B. Methyl N-({[1-(tert-butoxycarbonyl)piperidin-4-yl]amino}carbonyl)-O-[tert-butyl(diphenyl)silyl]serine 4-Amino-1-boc-piperidine (770 mg, 3.85 mmol) and triethylamine (0.536 mL, 3.85 mmol) in tetrahydrofuran (5 mL) was added to a solution of p-nitrophenylchloroformate (775 mg, 3.85 mmol) in tetrahydrofuran (15 mL) at 0° C. After 1 h, additional triethylamine was added (1.07 mL, 7.7 mmol) along with methyl O-[tert-butyl(diphenyl)silyl]serinate (1.38 g, 3.85 mmol). The reaction warmed to ambient temperature and was then heated to 50° C. After 16 h, the mixture was concentrated and redissolved in ethyl acetate. The ethyl acetate layer was washed with saturated sodium bicarbonate solution (3×), water, brine, and dried over sodium sulfate. Purification by silica gel chromatography (100% dichloromethane→8% methanol {1% ammonium hydroxide}/dichloromethane) gave the title compound (1.8 g). MS 584.62 (M+1)

Step C. tert-Butyl 4-[({[2-{[tert-butyl(diphenyl)silyl]oxy}-1-(hydroxymethyl)ethyl]amino}carbonyl)amino]piperidine-1-carboxylate Lithium aluminum hydride (1 M, 0.703 mL, 0.703 mmol) was added to a solution of N-({[1-(tert-butoxycarbonyl)piperidin-4-yl]amino}carbonyl)-O-[tert-butyl(diphenyl)silyl]serine (373 mg, 0.639 mmol) in tetrahydrofuran (20 mL) at −78° C. The reaction was quenched with saturated ammonium chloride solution and partitioned between dichloromethane and saturated sodium bicarbonate solution. The organic layer was dried over sodium sulfate, filtered, and concentrated. Purification by silica gel chromatography (1%→8% methanol {1% ammonium hydroxide}/dichloromethane) gave the title compound (100 mg). MS 556.3 (M+1)

Step D. tert-Butyl 4-[4-({[tert-butyl(diphenyl)silyl]oxy}methyl)-2-oxo-2,3-dihydro-1H-imidazol-1-yl]piperidine-1-carboxylate Dess-Martin periodinane (53 mg, 0.126 mmol) was added to a solution of tert-butyl 4-[({[2-{[tert-butyl(diphenyl)silyl]oxy}-1-(hydroxymethyl)ethyl]amino}carbonyl)amino]piperidine-1-carboxylate (50 mg, 0.090 mmol) in dichloromethane (20 mL) at 0° C. After 4 h, the reaction was quenched with a 1:1 mixture of saturated sodium thiosulfate and sodium bicarbonate solution. The mixture was extracted with dichloromethane (2×) and the combined organic extracts were dried over sodium sulfate, filtered, concentrated. Purification by silica gel chromatography (100% dichloromethane→9% methanol {1% ammonium hydroxide)/dichloromethane} gave the title compound (25 mg). MS 536.3 (M+1)

Step E. 4-(Hydroxymethyl)-1-piperidin-4-yl-1,3-dihydro-2H-imidazol-2-one

Trifluoroacetic acid (5 mL) was added to a solution of tert-butyl 4-[4-({[tert-butyl(diphenyl)silyl]oxy}methyl)-2-oxo-2,3-dihydro-1H-imidazol-1-yl]piperidine-1-carboxylate (550 mg, 1.03 mmol) in dichloromethane (15 mL). After 30 min, the reaction was concentrated to give the title compound.

Intermediate 13

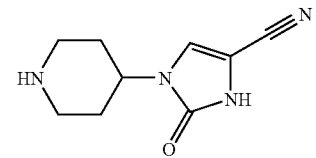

2-Oxo-1-piperidin-4-yl-2,3-dihydro-1H-imidazole-4-carbonitrile

Step A. Methyl N-({[1-(tert-butoxycarbonyl)piperidin-4-yl]amino}carbonyl)serinate 4-Amino-1-boc-piperidine (600 mg, 3.0 mmol) and triethylamine (0.417 mL, 3.0 mmol) in tetrahydrofuran (16 mL) were added to a solution of p-nitrophenylchloroformate (604 mg, 3.0 mmol) at 0° C. After 1 h, additional triethylamine was added (1.25 mL, 9 mmol) along with DL-serine methyl ester hydrochloride (571 mg, 4.79 mmol) in dimethylformamide (5 mL). The reaction was heated to 50° C. for 16 h. The mixture was concentrated and redissolved in ethyl acetate. The ethyl acetate layer was washed with 1 N sodium hydroxide solution (3×), water, brine, and dried over sodium sulfate. Purification by silica gel chromatography (100% dichloromethane→8% methanol {1% ammonium hydroxide}/dichloromethane) gave the title compound (700 mg). MS 346.22 (M+1)

Step B. tert-Butyl 4-[4-(methoxycarbonyl)-2-oxo-2,3-dihydro-1H-imidazol-1-yl]piperidine-1-carboxylate Dess-Martin periodinane (1.77 g, 4.16 mmol) was added to a solution of methyl N-({[1-(tert-butoxycarbonyl)piperidin-4-yl]amino}carbonyl)serinate (1.15 g, 3.33 mmol) in dichloromethane (30 mL) at 0° C. and then warmed to ambient temperature. After 4 h, the reaction was quenched with a 1:1 mixture of saturated sodium thiosulfate and sodium bicarbonate solution. The mixture was extracted with dichloromethane (2×) and the combined organic extracts were dried over sodium sulfate, filtered, and concentrated. Purification by silica gel chromatography (100% dichloromethane→12% methanol {1% ammonium hydroxide}/dichloromethane) gave the title compound.

Step C. 1-[1-(tert-Butoxycarbonyl)piperidin-4-yl]-2-oxo-2,3-dihydro-1H-imidazole-4-carboxylic acid Lithium hydroxide (64 mg, 1.54 mmol) was added to a solution of tert-butyl 4-[4-(methoxycarbonyl)-2-oxo-2,3-dihydro-1H-imidazol-1-yl]piperidine-1-carboxylate (50 mg, 0.154 mmol) in methanol (10 mL). After 2 h, the reaction was quenched with saturated sodium bicarbonate solution and dichloromethane was added. The mixture was filtered and the filtrate was concentrated. Purification by silica gel chromatography (100% dichloromethane→25% methanol {1% ammonium hydroxide}/dichloromethane) gave the title compound (17 mg). MS 312.2 (M+1)

Step D. tert-Butyl 4-[4-(aminocarbonyl)-2-oxo-2,3-dihydro-1H-imidazol-1-yl]piperidine-1-carboxylate A solution of 1-[1-(tert-butoxycarbonyl)piperidin-4-yl]-2-oxo-2,3-dihydro-1H-imidazole-4-carboxylic acid (210 mg, 0.675 mmol), N-[3-(dimethylamino)propyl]-N'-ethylcarbodiimide hydrochloride (388 mg, 2.02 mmol), 1H-1,2,3-benzotriazol-1-ol hydrate (273 mg, 2.02 mmol), N,N-diisopropylethylamine (0.352 mL, 2.02 mmol), and ammonia (0.5 M, 2.02 mmol, 4.05 mL) were stirred at room temperature in dimethylformamide (10 mL). After 3 h, the reaction was worked up with dichloromethane and saturated sodium bicarbonate. The organic extracts were washed with brine, dried over sodium sulfate, filtered and concentrated. Purification by silica gel chromatography (100% dichloromethane→15% methanol {1% ammonium hydroxide}/dichloromethane) gave the title compound (78 mg). MS 255.2 (M+1-tert butyl)

Step E. tert-Butyl 4-(4-cyano-2-oxo-2,3-dihydro-1H-imidazol-1-yl)piperidine-1-carboxylate (Methoxycarbonylsulfamoyl)triethylammonium hydroxide, inner salt (179.7 mg, 0.754 mmol) was added to a solution of tert-butyl 4-[4-(aminocarbonyl)-2-oxo-2,3-dihydro-1H-imidazol-1-yl]piperidine-1-carboxylate (78 mg, 0.251 mmol) in dichloroethane (5 mL) and was heated to 50° C. After 1 h, the reaction was worked up with dichloromethane and saturated sodium bicarbonate. The organic extracts were washed with brine, dried over sodium sulfate, filtered and concentrated. Purification by silica gel chromatography (100% dichloromethane→5% methanol {1% ammonium hydroxide}/dichloromethane) gave the title compound (40 mg). MS 237.04 (M+1-tert butyl)

Step F. 2-Oxo-1-piperidin-4-yl-2,3-dihydro-1H-imidazole-4-carbonitrile

Trifluoroacetic acid (4 mL) was added to a solution of tert-butyl 4-(4-cyano-2-oxo-2,3-dihydro-1H-imidazol-1-yl)piperidine-1-carboxylate (25 mg, 0.086 mmol) in dichloromethane (6 mL). After 20 min, the reaction was concentrated to give the title compound. MS 193.3 (M+1)

Intermediate 14

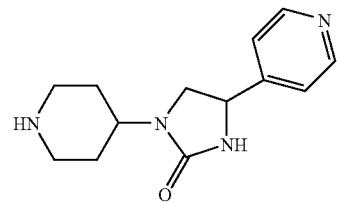

1-Piperidin-4-yl-4-pyridin-4-ylimidazolidin-2-one

Step A. Benzyl 4-[allyl(tert-butoxycarbonyl)amino]piperidine-1-carboxylate

Sodium triacetoxyborohydride (5.45 g, 25.72 mmol) was added to a solution of N-benzyloxycarbonyl-4-piperidone (5.0 g, 21.43 mmol), allylamine (1.77 mL, 23.58 mmol), and acetic acid (1.35 mL, 23.581 mmol) in dichloroethane (100 mL). After 1 h, the reaction was quenched with saturated sodium bicarbonate solution and extracted with dichloromethane (2×). The combined organics were washed with saturated potassium sodium tartrate solution, brine, dried over sodium sulfate, filtered, and concentrated. Di-tert-butyl dicarbonate (4.91 mg, 22.51 mmol) was then added to the crude amine and the mixture was heated at 55° C. for 30 min. The reaction was concentrated to give the title compound (8.75 g). MS 275.3 (M+1-boc group)

Step B. Benzyl 4-[(tert-butoxycarbonyl)(2-oxoethyl)amino]piperidine-1-carboxylate Ozone (g) was bubbled into a solution of benzyl 4-[allyl(tert-butoxycarbonyl)amino]piperidine-1-carboxylate (2.75 g, 7.34 mmol) in dichloromethane (30 mL) and methanol (15 mL) at −78° C. for 17 min. Nitrogen (g) was then bubbled into the mixture for 30 min followed by the addition of dimethylsulfide (2.70 mL, 36.72 mmol). The reaction warmed to ambient temperature and stirred for 3 h. The mixture was concentrated and redissolved in ethyl acetate. The ethyl acetate layer was washed with water (2×), brine (2×), dried over sodium sulfate, filtered, and concentrated to give the title compound (2.5 g). MS 277.09 (M+1-boc group)

Step C. Benzyl 4-((tert-butoxycarbonyl){(2E)-2-[(tert-butylsulfinyl)imino]ethyl}amino)piperidine-1-carboxylate 2-Methyl-2-propanesulfinamide (212 mg, 1.753 mmol) and cupric sulfate monohydrate (849 mg, 4.78 mmol) were added to a solution of benzyl 4-[(tert-butoxycarbonyl)(2-oxoethyl)amino]piperidine-1-carboxylate (600 mg, 1.59 mmol) in dichloroethane (15 mL) and was heated at 50° C. After 18 h, the reaction was filtered, concentrated, and purified by silica gel chromatography chromatography (75%-95% ethyl acetate/hexanes) to give the title compound (400 ing). MS 380.24 (M+1-boc group)

Step D. Benzyl 4-((tert-butoxycarbonyl){2-[(tert-butylsulfinyl)amino]-2-pyridin-4-ylethyl}amino)piperidine-1-carboxylate 4-Bromopyridine (360 mg, 2.28 mmol) in ether (5 mL) was added dropwise to a solution of n-butyllithium (2.5 M, 1.0 μL, 2.5 mmol) in ether (15 mL) at −78° C. After 30 min, benzyl 4-((tert-butoxycarbonyl) {(2E)-2-[(tert-butylsulfinyl)imino]ethyl}amino)piperidine-1-carboxylate (364 mg, 0.759 mmol) in ether (6 mL) was added to the mixture. After 1 h, the reaction was warmed to ambient temperature, quenched with saturated ammonium chloride solution (2 mL), and partitioned between dichloromethane and saturated sodium bicarbonate solution. The organic layer was washed with brine, dried over sodium sulfate, filtered, and concentrated. Purification by silica gel chromatography chromatography (75%-100% ethyl acetate/hexanes) to give the title compound (230 mg). MS 559.2 (M+1)

Step E. Benzyl 4-[(2-amino-2-pyridin-4-ylethyl)amino]piperidine-1-carboxylate Trifluoroacetic acid (5 mL) was added to a solution of benzyl 4-((tert-butoxycarbonyl){2-[(tert-butylsulfinyl)amino]-2-pyridin-4-ylethyl}amino)piperidine-1-carboxylate (230 mg, 0.412 mmol) in dichloromethane (10 mL). After 1 h, the reaction was concentrated, dissolved in methanol (5 μL), and treated with 4 N HCl in dioxane (4.12 mmol). After 1 h, the reaction was concentrated to give the title compound. MS 355.2 (M+1)

Step F. Benzyl 4-(2-oxo-4-pyridin-4-ylimidazolidin-1-yl)piperidine-1-carboxylate N,N'-Carbonyldiimidazole (160 mg, 0.987 mmol) and N,N-diisopropylethylamine (0.232 mL, 1.3 mmol) were added to a solution of benzyl 4-[(2-amino-2-pyridin-4-ylethyl)amino]piperidine 1-carboxylate (140 mg, 0.95 mmol) in acetonitrile (5 mL). After 16 h, the reaction was concentrated and partitioned between dichloromethane and saturated sodium bicarbonate solution. The organic layer was washed with brine, dried over sodium sulfate, filtered, and concentrated. Purification by silica gel chromatography chromatography (100% dichloromethane=10% methanol {1% ammonium hydroxide}/dichloromethane) gave the title compound (82 mg). MS 381.1 (M+1)

Step G. 1-Piperidin-4-yl-4-pyridin-4-ylimidazolidin-2-one

A solution of benzyl 4-(2-oxo-4-pyridin-4-ylimidazolidin-1-yl)piperidine-1-carboxylate (55 mg, 0.145 mmol) in ethanol (15 mL) was hydrogenated at 1 atm hydrogen over palladium on carbon (50 mg). After 16 h, the reaction was filtered and concentrated to give the title product. MS 247.2 (M+1)

Essentially following the procedures outlined for the foregoing Intermediate, the compounds listed in Table 2 were prepared.

TABLE 2

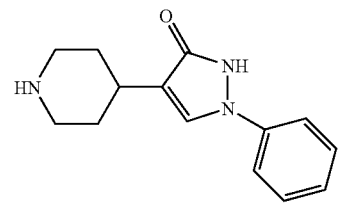

| Int. | R | MS (M + 1) |
|---|---|---|
| 15L-238634 | (pyridin-2-yl) | 247.3 |
| 16L-251624 | (pyridin-3-yl) | 247.2 |

Intermediate 17

1-Phenyl-4-piperidin-4-yl-1,2-dihydro-3H-pyrazol-3-one

Step A. N'-Phenyl-2-pyridin-4-ylacetohydrazide

N-[3-(dimethylamino)propyl]-N'-ethylcarbodiimide hydrochloride (2.06 g, 10.76 mmol, 2.02 mmol), 1H-1,2,3-benzotriazol-1-ol hydrate (1.45 g, 10.76 mmol), N,N-diisopropylethylamine (4.69 mL, 26.9 mmol), and phenyl hydrazine (970 mg, 8.97 mmol) were added to a solution of 4-pyridylacetic acid hydrochloride (1.23 g, 8.97 mmol) in dimethylformamide (10 mL). After 16 h, the reaction was worked up with dichloromethane and saturated sodium bicarbonate. The organic extracts were washed with brine, dried over sodium sulfate, filtered and concentrated. Purification by silica gel chromatography (99% dichloromethane→12% methanol {1% ammonium hydroxide}/dichloromethane) gave the title compound (400 mg). MS 228.5 (M+1)

Step B. 1-Phenyl-4-pyridin-4-yl-1,2-dihydro-3H-pyrazol-3-one

N'-Phenyl-2-pyridin-4-ylacetohydrazide (460 mg, 2.02 mmol) and calcium hydride (141 mg, 3.34 mmol) were dissolved in dimethylformamide (8 mL) and heated at 170° C. After 8 h, the reaction cooled to ambient temperature and was filtered. The mixture was concentrated and redissolved in dichloromethane (50 mL). The precipitate was filtered and dried under high vacuum overnight to give the desired product. MS 238.04 (M+1)

Step C. 1-Phenyl-4-piperidin-4-yl-1,2-dihydro-3H-pyrazol-3-one

Platinum oxide (60 mg) was added to a solution of 1-phenyl-4-pyridin-4-yl-1,2-dihydro-3H-pyrazol-3-one (180 mg, 0.758 mmol) in acetic acid (12 mL), concentrated hydrochloric acid (0.100 mL), and water (5 mL). The reaction vessel was evacuated and back-filled with nitrogen (3×), then back-filled with hydrogen (50 psi). After 5 h the mixture was filtered and concentrated to give the title compound. MS 244.3 (M+1).

Example 1

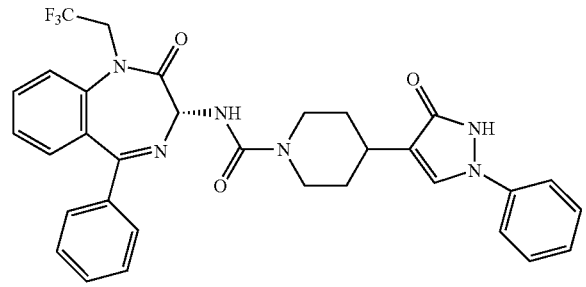

4-(3-Oxo-1-phenyl-2,3-dihydro-1H-pyrazol-4-yl)-N-[(3R)-2-oxo-5-phenyl-1-(2,2,2-trifluoroethyl)-2,3-dihydro-1H-1,4-benzodiazepin-3-yl]piperidine-1-carboxamide (3R)-3-Amino-5-phenyl-1-(2,2,2-trifluoroethyl)-1,3-dihydro-2H-1,4-benzodiazepin-2-one (137 mg, 0.411 mmol) (Y.-J. Shi et al., Tetrahedron, 1999, 55, 909-918) and triethylamine (0.057 mL, 0.411 mmol) were added to a solution of p-nitrophenylchloroformate (83 mg, 0.411 mmol) in tetrahydrofuran (20 mL) at 0° C. After 1 h, 1-phenyl-4-piperidin-4-yl-1,2-dihydro-3H-pyrazol-3-one (50 mg, 0.205 mmol) and additional triethylamine (0.171 mL, 1.23 mmol) were added and the reaction warmed to ambient temperature and was then heated at 50° C. After 4 h, the reaction was concentrated and partitioned between ethyl acetate and saturated sodium bicarbonate. The organics were washed with water, brine, and dried over magnesium sulfate. Purification by silica gel chromatography (100% dichloromethane→10% methanol {1% ammonium hydroxide}/dichloromethane) gave the title compound (27 mg). MS 603.23 (M+1)

Example 2

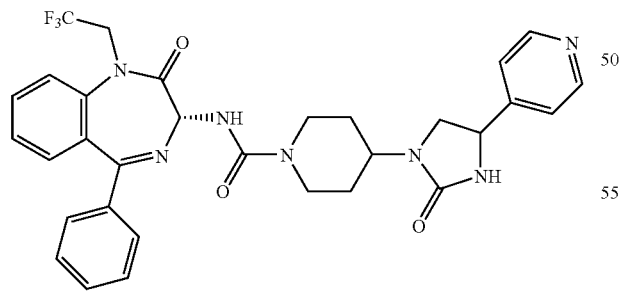

N-[(3R)-2-oxo-5-phenyl-1-(2,2,2-trifluoroethyl)-2,3-dihydro-1H-1,4-benzodiazepin-3-yl]-4-(2-oxo-4-pyridin-4-ylimidazolidin-1-yl)piperidine-1-carboxamide (3R)-3-Amino-5-phenyl-1-(2,2,2-trifluoroethyl)-1,3-dihydro-2H-1,4-benzodiazepin-2-one (49 mg, 0.146 mmol) (Y.-J. Shi et al., Tetrahedron, 1999, 55, 909-918) and triethylamine (0.020 mL, 0.146 mmol) were added to a solution of p-nitrophenylchloroformate (29 mg, 0.146 mmol) in tetrahydrofuran (5 mL) at 0 oC. After 1 h, 1-piperidin-4-yl-4-pyridin-4-ylimidazolidin-2-one (36 mg, 0.146 mmol) and additional triethylamine (0.040 mL, 0.292 mmol) were added and the reaction warmed to ambient temperature. After 16 h, the reaction was concentrated and partitioned between dichloromethane and saturated sodium bicarbonate. The organics were washed with water, brine, and dried over magnesium sulfate. Purification by silica gel chromatography (100% dichloromethane→15% methanol {1% ammonium hydroxide}/dichloromethane) gave the title compound (36 mg). MS 606.2 (M+1)

Essentially following the procedures outlined for the foregoing Example, the compounds listed in Table 3 were prepared.

TABLE 3

| Ex. | R | MS (M + 1) |
|---|---|---|
| 3L-237 191 | 2-pyridyl | 606.24 |
| 4 | 3-pyridyl | 606.24 |

Example 5

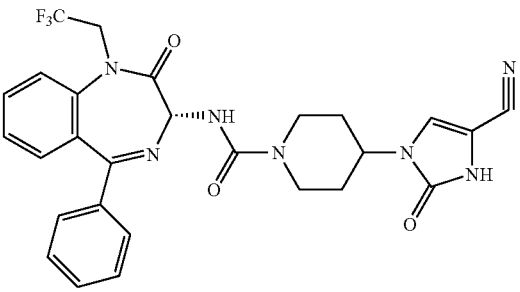

4-(4-Cyano-2-oxo-2,3-dihydro-1H-imidazol-1-yl)-N-[(3R)-2-oxo-5-phenyl-1-(2,2,2-trifluoroethyl)-2,3-dihydro-1H-1,4-benzodiazepin-3-yl]piperidine-1-carboxamide (3R)-3-Amino-5-phenyl-1-(2,2,2-trifluoroethyl)-1,3-dihydro-2H-1,4-benzodiazepin-2-one (38 mg, 0.114 mmol)

(Y.-J. Shi et al., Tetrahedron, 1999, 55, 909-918) and triethylamine (0.017 mL, 0.120 mmol) were added to a solution of p-nitrophenylchloroformate (23 mg, 0.114 mmol) in tetrahydrofuran (15 mL) at 0 oC. After 1 h, 2-oxo-1-piperidin-4-yl-2,3-dihydro-1H-imidazole-4-carbonitrile (23 mg, 0.120 mmol) and additional triethylamine (0.034 µL, 0.240 mmol) were added. The reaction warmed to ambient temperature and was then heated to 50 oC. After 2 h, the reaction was concentrated and then partitioned between dichloromethane and saturated sodium bicarbonate. The organics were washed with water, brine, and dried over magnesium sulfate. Purification by silica gel chromatography (100% dichloromethane→7% methanol {1% ammonium hydroxide}/dichloromethane) gave the title compound (40 mg). MS 552.195 (M+1)

Example 6

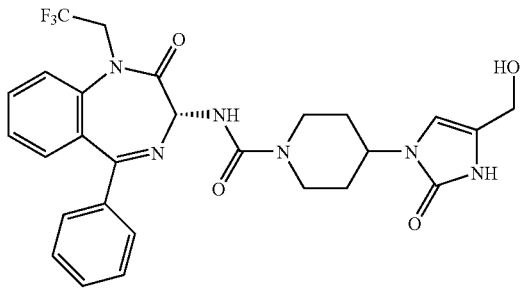

4-[4-(Hydroxymethyl)-2-oxo-2,3-dihydro-1H-imidazol-1-yl]-N-[(3R)-2-oxo-5-phenyl-1-(2,2,2-trifluoroethyl)-2,3-dihydro-1H-1,4-benzodiazepin-3-yl]piperidine-1-carboxamide (3R)-3-Amino-5-phenyl-1-(2,2,2-trifluoroethyl)-1,3-dihydro-2H-1,4-benzodiazepin-2-one (338 mg, 1.014 mmol) (Y.-J. Shi et al., Tetrahedron, 1999, 55, 909-918) and triethylamine (0.141 mL, 1.014 mmol) were added to a solution of p-nitrophenylchloroformate (204 mg, 1.014 mmol) in tetrahydrofuran (15 mL) at 0° C. After 1 h, 4-(hydroxymethyl)-1-piperidin-4-yl-1,3-dihydro-2H-imidazol-2-one (200 mg, 1.014 mmol) was added and the reaction stirred at 0 oC for 10 min and was then heated to 50 oC. After 4 h, the reaction was partitioned between ethyl acetate and saturated sodium bicarbonate and the organics were washed with water, brine, and dried over magnesium sulfate. Purification by preparative reverse phase chromatography gave the title compound (18 mg). MS 557.21 (M+1).

Example 7

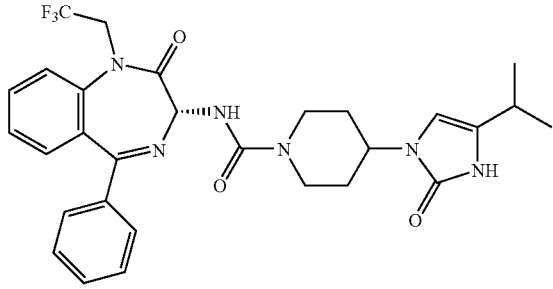

4-(4-Isopropyl-2-oxo-2,3-dihydro-1H-imidazol-1-yl)-N-[(3R)-2-oxo-5-phenyl-1-(2,2,2-trifluoroethyl)-2,3-dihydro-1H-1,4-benzodiazepin-3-yl]piperidine-1-carboxamide (3R)-3-Amino-5-phenyl-1-(2,2,2-trifluoroethyl)-1,3-dihydro-2H-1,4-benzodiazepin-2-one (127 mg, 0.382 mmol) (Y.-J. Shi et al., Tetrahedron, 1999, 55, 909-918) and triethylamine (0.053 mL, 0.382 mmol) were added to a solution of p-nitrophenylchloroformate (77 mg, 0.382 mmol) in tetrahydrofuran (45 mL) at 0° C. After 1 h, additional triethylamine was added (0.106 mL, 0.764 mmol) along with 4-isopropyl-1-piperidin-4-yl-1,3-dihydro-2H-imidazol-2-one (80 mg, 0.382 mmol). The reaction stirred at 0 oC for 10 min and was then heated to 50oC. After 2 h, the reaction was concentrated and redissolved in ethyl acetate. The organics were washed with 1 N sodium hydroxide solution (3×), water, brine, and dried over magnesium sulfate. Purification by silica gel chromatography (100% dichloromethane=10% methanol/dichloromethane) gave 100 mg of the titled compound. MS 569.24 (M+1).

Example 8

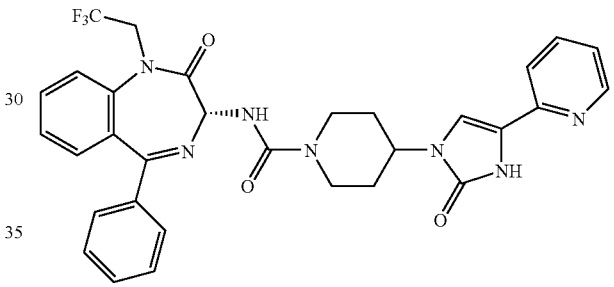

N-[(3R)-2-Oxo-5-phenyl-1-(2,2,2-trifluoroethyl)-2,3-dihydro-1H-1,4-benzodiazepin-3-yl]-4-(2-oxo-4-pyridin-2-yl-2,3-dihydro-1H-imidazol-1-yl)piperidine-1-carboxamide Step A. Ethyl amino(pyridin-2-yl)acetate 10% Palladium on carbon (100 mg) was added to a solution of ethyl (2Z)-(hydroxyimino)(pyridin-2-yl)ethanoate (592 mg, 2.67 mmol) in ethanol (20 mL). The reaction vessel was evacuated and back-filled with nitrogen (3×), then back-filled with hydrogen (1 atm). After 3 h, the mixture was filtered and concentrated to give the title compound (500 mg). MS 181.17 (M+1)

Step B. tert-Butyl 4-({[[(2-ethoxy-2-oxo-1-pyridin-2-ylethyl)amino]carbonyl} amino)piperidine-1-carboxylate 4-Amino-1-boc-piperidine (302 mg, 1.51 mmol) and triethylamine (0.210 mL, 1.51 mmol) in tetrahydrofuran (5 mL) were added to a solution of p-nitrophenylchloroformate (970 mg, 4.8 mmol) in tetrahydrofuran (15 mL) at 0° C. After 1 h, additional diisopropylethylamine was added (0.420 mL, 3.02 mmol) along with ethyl amino(pyridin-2-yl)acetate (272 mg, 1.51 mmol). The reaction was warmed to room temperature and stirred overnight. The mixture was filtered, concentrated and redissolved in ethyl acetate. The ethyl acetate layer was washed with 1N sodium hydroxide (3×), saturated sodium bicarbonate solution, water, brine, and dried over sodium sulfate. Purification by silica gel chromatography (100% dichloromethane→10% methanol {1% ammonium hydroxide}/dichloromethane) gave the title compound (330 mg). MS 407.29 (M+1)

Step C. Ethyl {[(piperidin-4-ylamino)carbonyl]amino} (pyridin-2-yl)acetate

Diisobutylaluminum hydride (1 M, 0.443 mL, 0.443 mmol) was added to a solution of tert-butyl 4-({[[(2-ethoxy-2-oxo-1-pyridin-2-ylethyl)amino]carbonyl} amino)piperidine-1-carboxylate (150 mg, 0.369 mmol) in toluene (5 μL) and dichloromethane (5 mL) at −78° C. and stirred for 30 min and then warmed to ambient temperature. After 4 h, the reaction was quenched with 1 N saturated potassium sodium tartrate solution (20 mL) and extracted with dichloromethane (2×). The combined organic extracts were dried over sodium sulfate, filtered, concentrated. The crude material was dissolved in dichloromethane (5 μL) and treated with trifluoroacetic acid (5 mL). After 30 min, the reaction was concentrated to give the title compound. MS 307.3 (M+1)

Step D. Ethyl [({1-({[[(3R)-2-oxo-5-phenyl-1-(2,2,2-trifluoroethyl)-2,3-dihydro-1H-1,4-benzodiazepin-3-yl]amino}carbonyl)piperidin-4-yl]amino}carbonyl) amino](pyridin-2-yl)acetate (3R)-3-Amino-5-phenyl-1-(2,2,2-trifluoroethyl)-1,3-dihydro-2H-1,4-benzodiazepin-2-one (90 mg, 0.270 mmol) (Y.-J. Shi et al., Tetrahedron, 1999, 55, 909-918) and triethylamine (37 uL, 0.270 mmol) in tetrahydrofuran (3 mL) were added to a solution of p-nitrophenylchloroformate (54 mg, 0.270 mmol) in tetrahydrofuran (15 mL) at 0° C. After 1 h, additional triethylamine (74 uL, 0.540 mmol) and ethyl {[(piperidin-4-ylamino)carbonyl]amino}(pyridin-2-yl)acetate (100 mg, 0.598 mmol) in tetrahydrofuran (5 μL) and dimethyl formamide (1 mL) were added and stirred at 0 oC for 10 min and then warmed to room temperature. After 4 h, the reaction was concentrated and the residue dissolved in ethyl acetate, washed with 1 N sodium hydroxide solution (3×), water, brine, and dried over magnesium sulfate. Purification by silica gel chromatography (100% dichloromethane→12% methanol/dichloromethane) gave 70 mg of the titled compound.

Step E. N-[(3R)-2-oxo-5-phenyl-1-(2,2,2-trifluoroethyl)-2,3-dihydro-1H-1,4-benzodiazepin-3-yl]-4-(2-oxo-4-pyridin-2-yl-2,3-dihydro-1H-imidazol-1-yl) piperidine-1-carboxamide Diisobutylaluminum hydride (1M, 0.108 mL, 0.108 mmol) was added to a solution of ethyl [({1-({[[(3R)-2-oxo-5-phenyl-1-(2,2,2-trifluoroethyl)-2,3-dihydro-1H-1,4-benzodiazepin-3-yl]amino}carbonyl)piperidin-4-yl]amino}carbonyl) amino](pyridin-2-yl)acetate (60 mg, 0.090 mmol) in toluene (4 mL) and dichloromethane (4 mL) at −78° C. and stirred for 30 min and then warmed to ambient temperature. After 4 h, the reaction was quenched with 1 N saturated potassium sodium tartrate solution and extracted with dichloromethane (2×). The combined organic extracts were dried over sodium sulfate, filtered, concentrated. Purification by silica gel chromatography (100% dichloromethane→10% methanol {1% ammonium hydroxide}/dichloromethane) gave the title compound. MS 604.2 (M+1)

Example 9

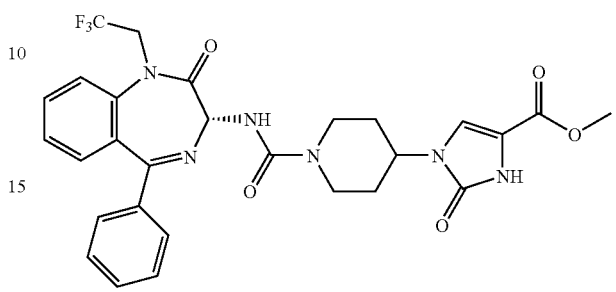

Methyl 2-oxo-1-[1-({[[(3R)-2-oxo-5-phenyl-1-(2,2,2-trifluoroethyl)-2,3-dihydro-1H-1,4-benzodiazepin-3-yl]amino}carbonyl)piperidin-4-yl]-2,3-dihydro-1H-imidazole-4-carboxylate

Step A. 4-Amino-N-[(3R)-2-oxo-5-phenyl-1-(2,2,2-trifluoroethyl)-2,3-dihydro-1H-1,4-benzodiazepin-3-yl]piperidine-1-carboxamide (3R)-3-amino-5-phenyl-1-(2,2,2-tirifluoroethyl)-1,3-dihydro-2H-1,4-benzodiazepin-2-one (1.71 g, 5.13 mmol) (Y.-J. Shi et al., Tetrahedron, 1999, 55, 909-918) and triethylamine (715 uL, 5.13 mmol) were added to a solution of p-nitrophenylchloroformate (1.03 g, 5.13 mmol) in tetrahydrofuran (45 mL) at 0 oC. After 1 h, additional triethylamine (1.43 mL, 10.26 mmol) and 4-boc-amino-piperidine (1.03 g, 5.13 mmol) were added and stirred at 0 oC for 10 min and then warmed to room temperature. After 16 h, the reaction was concentrated and the residue dissolved in ethyl acetate, washed with 1 N sodium hydroxide solution (3×), water, brine, and dried over magnesium sulfate. The crude material was purified by silica gel chromatography (100% dichloromethane→10% methanol/dichloromethane). 4 N HCl in dioxane (20 mL) was added to the boc protected compound in methanol (10 mL). After 16 h, the reaction was partitioned between ethyl acetate and saturated sodium bicarbonate. The organic layer was dried over magnesium sulfate, filtered, and concentrated to give the title compound (2 g). MS 460.2 (M+1)

Step B. Methyl N-({[1-({[[(3R)-2-oxo-5-phenyl-1-(2,2,2-trifluoroethyl)-2,3-dihydro-1H-1,4-benzodiazepin-3-yl]amino}carbonyl)piperidin-4-yl] amino}carbonyl)serinate 4-Amino-N-[(3R)-2-oxo-5-phenyl-1-(2,2,2-trifluoroethyl)-2,3-dihydro-1H-1,4-benzodiazepin-3-yl]piperidine-1-carboxamide (323 mg, 0.703 mmol) and triethylamine (0.098 mL, 0.703 mmol) were added to a solution of p-nitrophenylchloroformate (142 mg, 0.703 mmol) in tetrahydrofuran(15 μL) at 0° C. After 20 min, diisopropylethylamine was added (0.404 mL, 2.32 mmol) along with 2-amino-3-hydroxy-propionic acid methyl ester (251 mg, 2.32 mmol). The reaction was warmed to room temperature and stirred for 30 min and was then heated to 50° C. After 2 h, the mixture was concentrated and redissolved in ethyl acetate. The ethyl acetate layer was washed with 1N sodium hydroxide (3×), water, brine, and dried over sodium sulfate. Purification by silica gel chromatography (99% dichloromethane→15% methanol {1% ammonium hydroxide}/dichloromethane) gave the title compound (350 mg). MS 605.2 (M+1)

Step C. Methyl 2-oxo-1-[1-({[(3R)-2-oxo-5-phenyl-1-(2,2,2-trifluoroethyl)-2,3-dihydro-1H-1,4-benzodiazepin-3-yl]amino}carbonyl)piperidin-4-yl]-2,3-dihydro-1H-imidazole-4-carboxylate Dess-Martin periodinane (126 mg, 0.298 mmol) was added to a solution of methyl N-({[1-({[(3R)-2-oxo-5-phenyl-1-(2,2,2-trifluoroethyl)-2,3-dihydro-1H-1,4-benzodiazepin-3-yl]amino}carbonyl)piperidin-4-yl]amino}carbonyl)serinate (75 mg, 0.124 mmol) in dichloromethane (15 mL) at 0° C. The reaction warmed to ambient temperature, stirred for 4 h, and was quenched with a 1:1 mixture of saturated sodium thiosulfate and sodium bicarbonate solution. The mixture was extracted with dichloromethane (2×) and the combined organic extracts were dried over sodium sulfate, filtered, concentrated. Purification by silica gel chromatography (100% dichloromethane→8% methanol {1% ammonium hydroxide}/dichloromethane) gave the title compound (55 mg). MS 585.4 (M+1)

Example 10

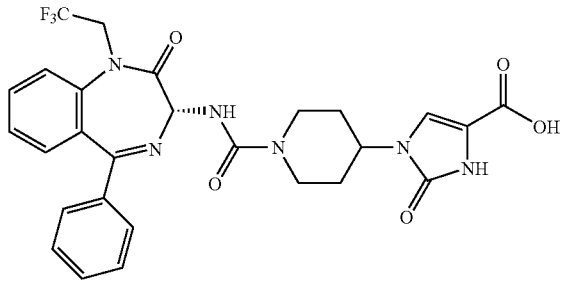

2-Oxo-1-[1-({[(3R)-2-oxo-5-phenyl-1-(2,2,2-trifluoroethyl)-2,3-dihydro-1H-1,4-benzodiazepin-3-yl]amino}carbonyl)piperidin-4-yl]-2,3-dihydro-1H-imidazole-4-carboxylic acid Lithium hydroxide (43 mg, 1.03 mmol) in water (2 mL) was added to a solution methyl 2-oxo-1-[1-({[(3R)-2-oxo-5-phenyl-1-(2,2,2-trifluoroethyl)-2,3-dihydro-1H-1,4-benzodiazepin-3-yl]amino}carbonyl)piperidin-4-yl]-2,3-dihydro-1H-imidazole-4-carboxylate (30 mg, 0.051 mmol) in methanol (2 mL) and heated to 40 o C. After 2 h, the reaction was purified by preparative reverse phase chromatography to give the title compound (5 mg). MS 571.2 (M+1)

Example 11

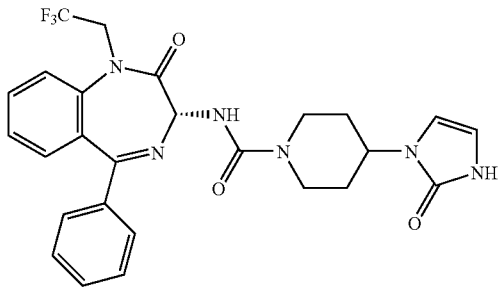

4-(2-Oxo-2,3-dihydro-1H-imidazol-1-yl)-N-[(3R)-2-oxo-5-phenyl-1-(2,2,2-trifluoroethyl)-2,3-dihydro-1H-1,4-benzodiazepin-3-yl] piperidine-1-carboxamide (3R)-3-Amino-5-phenyl-1-(2,2,2-trifluoroethyl) 1,3-dihydro-2H-1,4-benzodiazepin-2-one (199 mg, 0.598 mmol) (Y.-J. Shi et al., Tetrahedron, 1999, 55, 909-918) and triethylamine (83 uL, 0.598 mmol) in tetrahydrofuran (5 mL) were added to a solution of p-nitrophenylchloroformate (100 mg, 0.598 mmol) in tetrahydrofuran (15 mL) at 0 oC. After 1 h, 1-piperidin-4-yl-1,3-dihydro-2H-imidazol-2-one (100 mg, 0.598 mmol) in tetrahydrofuran (9 mL) and dimethylforamide (1 mL) were added and stirred at 0 oC for 10 min and then warned to room temperature. After 16 h, the reaction was concentrated and the residue dissolved in ethyl acetate, washed with 1 N sodium hydroxide solution (3×), water, brine, and dried over magnesium sulfate. Purification by silica gel chromatography (100% dichloromethane→10% methanol/dichloromethane) gave 70 mg of the titled compound. MS 527.5 (M+1).

Example 12

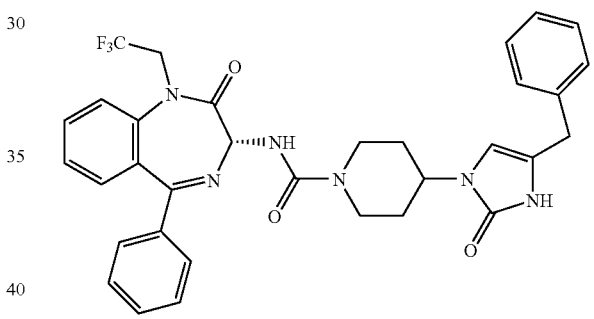

4-(4-Benzyl-2-oxo-2,3-dihydro-1H-imidazol-1-yl)-N-[(3R)-2-oxo-5-phenyl-1-(2,2,9-trifluoroethyl)-2,3-dihydro-1H-1,4-benzodiazepin-3-yl]piperidine-1-carboxamide (3R)-3-Amino-5-phenyl-1-(2,2,2-trifluoroethyl)-1,3-dihydro-2H-1,4-benzodiazepin-2-one (84 mg, 0.253 mmol) (Y.-J. Shi et al., Tetrahedron, 1999, 55, 909-918) and triethylamine (35 uL, 0.253 mmol) in tetrahydrofuran (10 mL) were added to a solution of p-nitrophenylchloroformate (51.0 mg, 0.253 mmol) in tetrahydrofuran (15 mL) at 0 oC. After 1 h, 4-benzyl-1-piperidin-4-yl-1,3-dihydro-2H-imidazol-2-one-fluorophenyl)-1-piperidin-4-ylimidazolidin-2-one (65 mg, 0.253 mmol) in tetrahydrofuran (20 μL) was added and stirred at 0 oC for 10 min and then warmed to room temperature. After 2 h, the reaction was concentrated and the residue dissolved in ethyl acetate, washed with saturated sodium bicarbonate, and dried over magnesium sulfate. Purification by silica gel chromatography (100% dichloromethane→10% methanol/dichloromethane) gave 55 mg of the titled compound. MS 617.25 (M+1).

Example 13

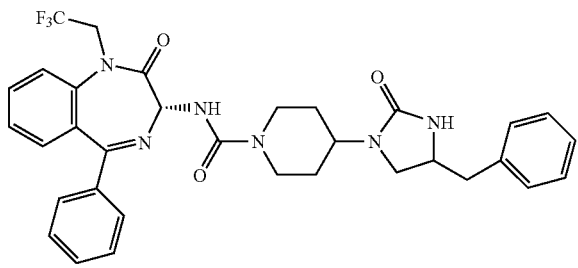

4-(4-Benzyl-2-oxoimidazolidin-1-yl)-N-[(3R)-2-oxo-5-phenyl-1-(2,2,2-trifluoroethyl)-2,3-dihydro-1H-1,4-benzodiazepin-3-yl]piperidine-1-carboxamide (3R)-3-Amino-5-phenyl-1-(2,2,2-trifluoroethyl)-1,3-dihydro-2H-1,4-benzodiazepin-2-one (23 mg, 0.069 mmol) (Y.-J. Shi et al., Tetrahedron, 1999, 55, 909-918) and triethylamine (0.009 μL, 0.069 mmol) were added to a solution of p-nitrophenylchloroformate (14 mg, 0.069 mmol) in tetrahydrofuran (15 mL) at 0 oC. After 1 h, 4-benzyl-1-piperidin-4-ylimidazolidin-2-one (18 mg, 0.069 mmol) and additional triethylamine (0.027 mL, 0.207 mmol) were added and the reaction warmed to ambient temperature. After 16 h, the reaction was concentrated and partitioned between ethyl acetate and 1 N sodium hydroxide solution. The organics were washed with water, brine, and dried over magnesium sulfate. Purification by silica gel chromatography (100% dichloromethane=9% methanol {1% ammonium hydroxide}/dichloromethane) gave the title compound (30 mg). MS 619.6 (M+1)

Example 14 and 14A

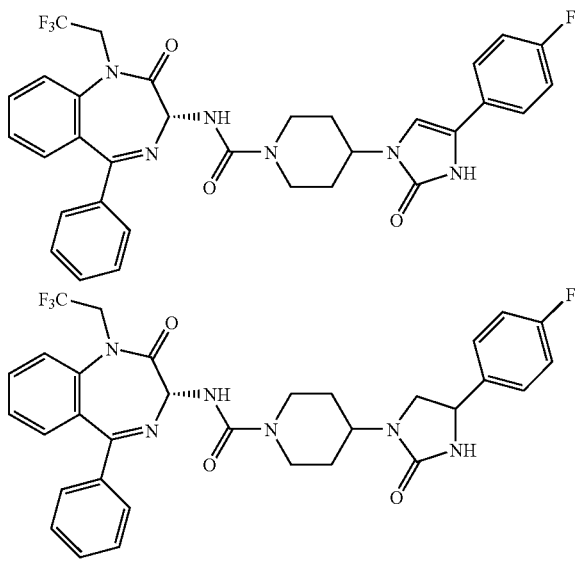

4-[4-(4-Fluorophenyl)-2-oxo-2,3-dihydro-1H-imidazol-1-yl]-N-[(3R)-2-oxo-5-phenyl-1-(2,2,2-trifluoroethyl)-2,3-dihydro-1H-1,4-benzodiazepin-3-yl]piperidine-1-carboxamide and 4-[4-(4-fluorophenyl)-2-oxoimidazolidin-1-yl]-N-[(3R)-2-oxo-5-phenyl-1-(2,2,2-trifluoroethyl)-2,3-dihydro-1H-1,4-benzodiazepin-3-yl]piperidine-1-carboxamide (3R)-3-Amino-5-phenyl-1-(2,2,2-trifluoroethyl)-1,3-dihydro-2H-1,4-benzodiazepin-2-one (74 mg, 0.22 mmol) (Y.-J. Shi et al., Tetrahedron, 1999, 55, 909-918) and triethylamine (31 uL, 0.22 mmol) in tetrahydrofuran (10 mL) were added to a solution of p-nitrophenylchloroformate (44.8 mg, 0.22 mmol) in tetrahydrofuran (15 mL) at 0 oC. After 1 h, additional triethylamine was added (62 uL, 0.44 mmol) along with the mixture of 4-(4-fluorophenyl)-1-piperidin-4-yl-1,3-dihydro-2H-imidazol-2-one and 4-(4-fluorophenyl)-1-piperidin-4-ylimidazolidin-2-one (58 mg, 0.222 mmol). The reaction was warmed to room temperature and stirred for 2 h. The reaction was concentrated and the residue dissolved in ethyl acetate, washed with saturated sodium bicarbonate, and dried over magnesium sulfate. Purification by silca gel chromatography (100% dichloromethane→10% methanol/dichloromethane) gave 45 mg of the unsaturated compound and 38 mg of the saturated compound. MS 621.3 and 623.3, respectively (M+1).

Example 15

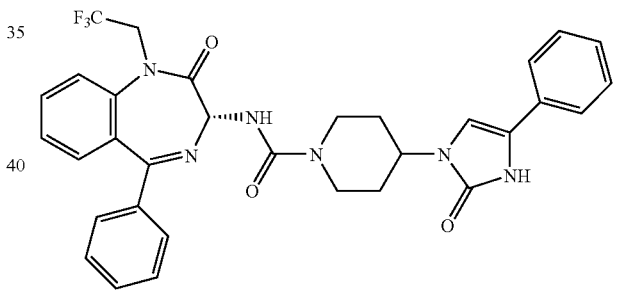

N-[(3R)-2-Oxo-5-phenyl-1-(2,2,2-trifluoroethyl)-2,3-dihydro-1H-1,4-benzodiazepin-3-yl]-4-(2-oxo-4-phenyl-2,3-dihydro-1H-imidazol-1-yl)piperidine-1-carboxamide (3R) 3-Amino-2-oxo-5-phenyl-1-(2,2,2-trifluoroethyl)-2,3-dihydro-1H-1,4-benzodiazepine (20.0 mg, 0.06 mmol) (Y.-J. Shi et al., Tetrahedron, 1999, 55, 909-918) and p-nitrophenylchloroformate (12.1 mg, 0.06 mmol) were dissolved in tetrahydrofuran (0.5 mL) under argon, and cooled to 0° C. Triethylamine (19 uL, 0.14 mmol) was added and the reaction stirred for 1 h, followed by addition of more triethylamine (19 uL) and 4-phenyl-1-piperidin-4-yl-1,3-dihydro-2H-imidazol-2-one hydrochloride (16.8 mg, 0.06 mmol), prepared according to the procedure described in the patent U.S. Pat. No. 6,344,449 B1. The reaction was warmed to room temperature and stirred overnight. The crude product was purified by reverse phase HPLC (C-18, 5% to 95% 0.1% trifluoroacetic acid/acetonitrile in 0.1% aqueous trifluoroacetic acid gradient elution) to give she title compound (26.1 mg). MS 603 (M+1)

L-236640

L-251630

Essentially following the procedures outlined for the foregoing Example, the compounds listed in Table 4 were prepared.

TABLE 4

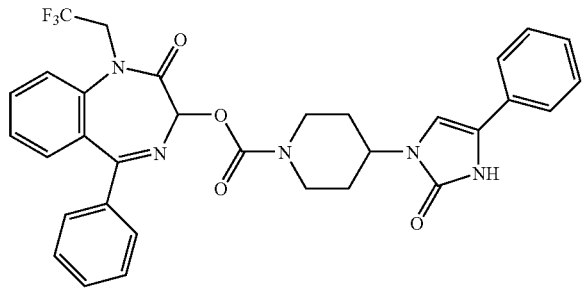

| Ex. | R | MS (M + 1) |
|---|---|---|
| 16 L-237191 | 4-CH3 | 617.2485 |
| 17 L-238634 | 4-OCH3 | 633.2457 |
| 18 L-251624 | 4-OCF3 | 687.2170 |
| 19 | 4-OCHF2 | 669.2268 |
| 20 | 3-OCH3 | 633.2462 |
| 21 | 3-F | 621.2220 |

Example 22

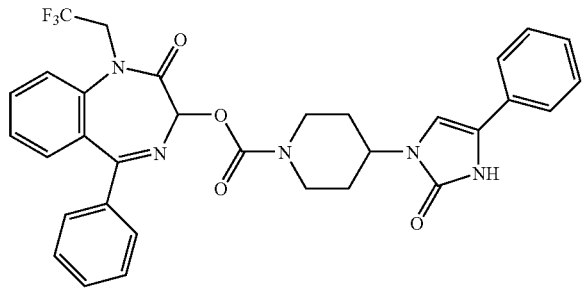

(3R)-2-Oxa-5-phenyl-1-(2,2,2-trifluoroethyl)-2,3-dihydro-1H-1,4-benzodiazepin-3-yl 4-(2-oxo-4-phenyl-2,3-dihydro-1H-imidazol-1-yl)piperidine-1-carboxylate 3-Hydroxy-2-oxo-5-phenyl-1-(2,2,2-trifluoroethyl)-2,3-dihydro-1H-1,4-benzodiazepine (1.0 g, 2.99 mmol) and p-nitrophenylchloroformate (0.66 g, 3.29 mmol) were dissolved in tetrahydrofuran (40 mL) under argon, and cooled to 0 oC. Triethylamine (373 uL, 2.69 mmol) was added and the reaction stirred for 1 h. More p-nitrophenylchloroformate (0.090 g, 0.45 mmol) was added, and reaction stirred 1 h. Additional triethylamine was added (830 uL, 5.98 mmol) along with 4-phenyl-1-piperidin-4-yl-1,3-dihydro-2H-imidazol-2-one hydrochloride (837 mg, 2.99 mmol). The reaction was warmed to room temperature and stirred overnight. The reaction was concentrated and the residue dissolved in methylene chloride, washed with saturated sodium bicarbonate and brine, and dried over magnesium sulfate. The crude solid was purified by column chromatography (silica gel, 0 to 10% {5% ammonium hydroxide/methanol} in methylene chloride gradient elution). A second purification was accomplished by reverse phase HPLC (C-18, 5% to 95% 0.1% trifluoroacetic acid/acetonitrile in 0.1% aqueous trifluoroacetic acid gradient elution) to give the title compound (820 mg). MS 604.2155 (M+1)

Example 23

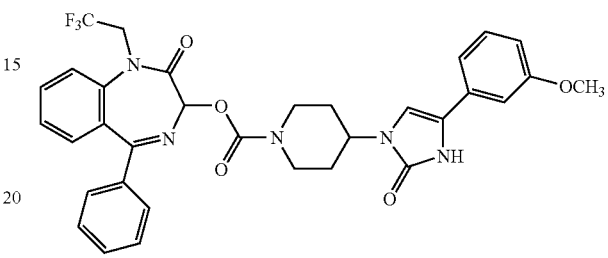

(3R)-2-Oxo-5-phenyl-1-(2,2,2-trifluoroethyl)-2,3-dihydro-1H-1,4-benzodiazepin-3-yl 4-[2-oxo-4-(3-methoxyphenyl)-2,3-dihydro-1H-imidazol-1-yl]piperidine-1-carboxylate The title compound was prepared in the same way as (3R)-2-oxo-5-phenyl-1-(2,2,2-trifluoroethyl)-2,3-dihydro-1H-1,4-benzodiazepin-3-yl 4-(2-oxo-4-phenyl-2,3-dihydro-1H-imidazol-1-yl)piperidine-1-carboxylate, except using 4-(3-methoxyphenyl)-1-piperidin-4-yl-1,3-dihydro-2H-imidazol-2-one hydrochloride in place of 4-phenyl-1-piperidin-4-yl-1,3-dihydro-2H-imidazol-2-one hydrochloride. MS 634.2266 (M+1)

Example 24

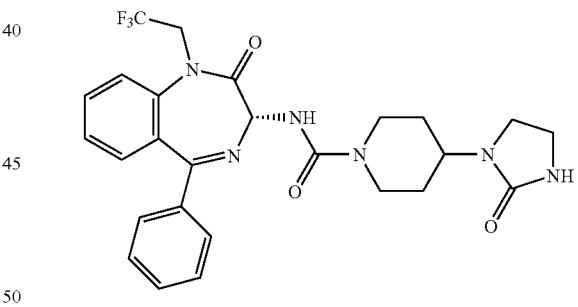

N-[3R)-2-Oxo-5-phenyl-1-(2,2,2-trifluoroethyl)-2,3-dihydro-1H-1,4-benzodiazepin-3-yl]-4-(2-oxo-imidazolidin-1-yl)piperidine-1-carboxamide Step A. 4-Nitrophenyl [(3R)-2-oxo-5-phenyl-1-(2,2,2-trifluoroethyl)-2,3-dihydro-1H-1,4-benzodiazepin-3-yl]carbamate (3R) 3-Amino-2-oxo-5-phenyl-1-(2,2,2-trifluoroethyl)-2,3-dihydro-1H-1,4-benzodiazepine (1.21 g, 3.63 mmol) and p-nitrophenylchloroformate (201.5 mg, 3.63 mmol) were dissolved in tetrahydrofuran (30 mL) under argon, and cooled to 0° C. Triethylamine (0.48 mL, 0.3.45 mmol) was added and the reaction stirred for 1 h. The solution was filtered and concentrated to give the title compound as a light yellow solid (1.9 g).

Step B. N-[3R)-2-oxo-5-phenyl-1-(2,2,2-trifluoroethyl)-2,3-dihydro-1H-1,4-benzodiazepin-3-yl]-4-(2-oxo-imidazolidin-1-yl)piperidine-1-carboxamide 4-Nitrophenyl [(3R)-2-oxo-5-phenyl-1-(2,2,2-trifluoroethyl)-2,3-dihydro-1H-1,4-benzodiazepin-3-yl]carbamate (52.8 mg, 0.11 mmol) and 1-(piperidin-4-yl)imidazolidin-2-one (17.9 mg, 0.112 mmol) were dissolved in methylene chloride (1 mL) and triethylamine (40 uL, 0.32 mmol) added. The reaction was stirred overnight, concentrated, and purified by reverse phase HPLC (C-18, 5% to 95% 0.1% trifluoroacetic acid/acetonitrile in 0.1% aqueous trifluoroacetic acid gradient elution). Workup with ethyl acetate and saturated sodium bicarbonate gave the title compound (28 mg). MS 529.2162 (M+1)

Example 25

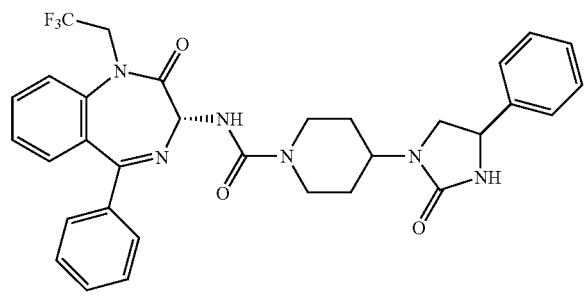

N-[(3R)-2-Oxo-5-phenyl-1-(2,2,2-trifluoroethyl)-2,3-dihydro-1H-1,4-benzodiazepin-3-yl]-4-(2-oxo-4-phenylimidazolidin-1-yl)piperidine-1-carboxamide (3R) 3-Amino-2-oxo-5-phenyl-1-(2,2,2-trifluoroethyl)-2,3-dihydro-1H-1,4-benzodiazepine (20.0 mg, 0.06 mmol) and p-nitrophenylchloroformate (12.1 mg, 0.06 mmol) were dissolved in tetrahydrofuran (0.5 mL) under argon, and cooled to 0° C. Triethylamine (8.4 uL, 0.06 mmol) was added and the reaction stirred for 1 h, followed by addition of more triethylamine (21 uL) and 4-phenyl-1-piperidin-4-ylimidazolidin-2-one trifluoroacetic acid salt (21.6 mg, 0.06 mmol), in dimethylsulfoxide (0.5 mL). The reaction was warmed to room temperature and stirred overnight. The crude product was purified by reverse phase HPLC (C-18, 5% to 95% 0.1% trifluoroacetic acid/acetonitrile in 0.1% aqueous trifluoroacetic acid gradient elution) to give the title compound (18.5 mg). MS 605.2459 (M+1)

Example 26

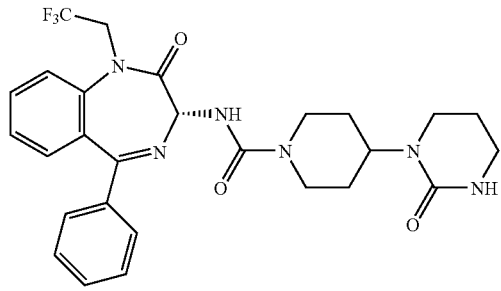

N-[3R)-2-Oxo-5-phenyl-1-(2,2,2-trifluoroethyl)-2,3-dihydro-1H-1,4-benzodiazepin-3-11]-4-(2-oxotetrahydropyrimidin-1[2H]-yl)piperidine-1-carboxamide Step A. 4-Nitrophenyl [(3R)-2-oxo-5-phenyl-1-(2,2,2-trifluoroethyl)-2,3-dihydro-1H-1,4-benzodiazepin-3-yl]carbamate (3R) 3-Amino-2-oxo-5-phenyl-1-(2,2,2-trifluoroethyl)-2,3-dihydro-1H-1,4-benzodiazepine (1.21 g, 3.63 mmol) and p-nitrophenylchloroformate (201.5 mg, 3.63 mmol) were dissolved in tetrahydrofuran (30 mL) under argon, and cooled to 0° C. Triethylamine (0.48 mL, 0.3.45 mmol) was added and the reaction stirred for 1 h. The solution was filtered and concentrated to give the title compound as a light yellow solid (1.9 g).

Step B. N-[3R)-2-Oxo-5-phenyl-1-(2,2,2-trifluoroethyl)-2,3-dihydro-1H-1,4-benzodiazepin-3-yl]-4-(2-oxotetrahydropyrimidin-1 [2H]-yl)piperidine-1-carboxamide 4-Nitrophenyl [(3R)-2-oxo-5-phenyl-1-(2,2,2-trifluoroethyl)-2,3-dihydro-1H-1,4-benzodiazepin-3-yl]carbamate (35.4 mg, 0.07 mmol) and 1-piperidinyl-4-yltetrahydropyrimidin-2[1H]-one (13 mg, 0.07 mmol) were dissolved in methylene chloride (2 mL) and triethylamine (30 uL, 0.21 mmol) added. The reaction was stirred overnight, concentrated, and purified by reverse phase HPLC (C-18, 5% to 95% 0.1% trifluoroacetic acid/acetonitrile in 0.1% aqueous trifluoroacetic acid gradient elution). Workup with ethyl acetate and saturated sodium bicarbonate gave the title compound (16 mg). MS 543.2323 (M+1)

Example 27

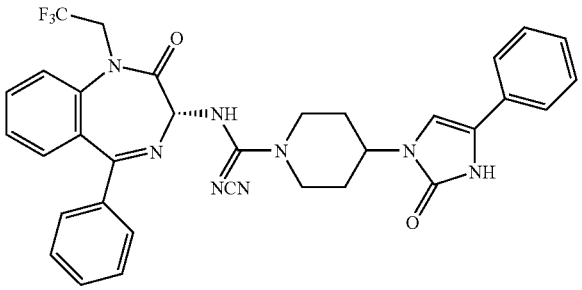

N'-Cyano-N-[(3R)-2-oxo-5-phenyl-1-(2,2,2-trifluoroethyl)-2,3-dihydro-1H-1,4-benzodiazepin-3-yl]-4-(2-oxo-4-phenyl-2,3-dihydro-1H-imidazol-1-yl)piperidine-1-carboximidamide Diisopropylethylamine (107 uL, 0.615 mmol) was added to a solution of (3R) 3-amino-2-oxo-5-phenyl-1-(2,2,2-trifluoroethyl)-2,3-dihydro-1H-1,4-benzodiazepine (205 mg, 0.615 mmol) and diphenyl N-cyanocarbonimidate (147 mg, 0.615 mmol) in methylene chloride (5 mL). The reaction was stirred at room temperature for 72 h, then quenched with 0.5 N sodium hydroxide. The methylene chloride was washed with water and saturated brine, and dried over sodium sulfate. The solid product (139 mg, 0.291 mmol) was dissolved in 1-pentanol (2 mL) along with 4-phenyl-1-piperidin-4-yl-1,3-dihydro-2H-imidazol-2-one hydrochloride (81.4 mg, 0.291 mmol) and diisopropylethylamine (76.1 uL, 0.437 mmol), and refluxed under argon overnight. An additional equivalent of 4-phenyl-1-piperidin-4-yl-1,3-dihydro-2H-imidazol-2-one hydrochloride was added and the reaction refluxed by silica gel chromatography (100% dichloromethane→10% methanol/dichloromethane) gave 55 mg of the titled compound. MS 617.25 (M+1). overnight. The reaction was concentrated and purified by chromatography (silica gel, 0-5% methanol in methylene chloride containing 0.1% ammonium hydroxide, gradient elution), providing the title compound. MS 627.2464 (M+1)

Example 28

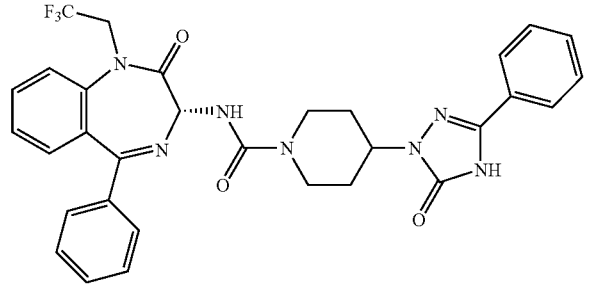

L-236640

N-[(3R)-2-Oxo-5-phenyl-1-(2,2,2-trifluoroethyl)-2,3-dihydro-1H-1,4-benzodiazepin-3-yl]-4-(5-oxo-3-phenyl-4,5-dihydro-1H-1,2,4-triazol-1-yl)piperidine-1-carboxamide (3R) 3-Amino-2-oxo-5-phenyl-1-(2,2,2-trifluoroethyl)-2,3-dihydro-1H-1,4-benzodiazepine (55.0 mg, 0.165 mmol) and p-nitrophenylchloroformate (33.3 mg, 0.165 mmol) were dissolved in tetrahydrofuran (1.0 mL) under argon, and cooled to 0° C. Triethylamine (23 uL, 0.165 mmol) was added and the reaction stirred for 1 h. Additional triethylamine was added (34.5 uL, 0.247 mmol) along with 5-phenyl-1-piperidin-4-yl-2,4-dihydro-3H-1,2,4-triazol-3-one hydrochloride (40.3 mg, 0.165 mmol) in dimethylsulfoxide (1 mL). The reaction was warmed to room temperature and stirred overnight. The mixture was partitioned between methylene chloride and 1N sodium hydroxide, and the organic extract washed with brine and dried over magnesium sulfate. The crude product was purified by column chromatography (silica gel, 0 to 10% {5% ammonium hydroxide/methanol} in methylene chloride gradient elution), giving the title compound as a white solid (86 mg). MS 604 (M+1) L-236640

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above.

What is claimed is:

1. A compound of Formula I:

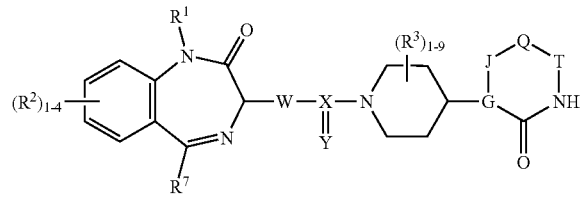

wherein:

R1 is selected from:

1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents independently selected from $R^4$,
  e) heterocycle, unsubstituted or substituted with 1-5 substituents independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) $CN$,
  t) $NR^{10}R^{11}$,
  u) $N(R^{10})(CO)NR^4 R^{11}$, and
  v) $O(CO)R^4$; and 2) aryl or heteroaryl, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents independently selected from $R^4$,
  e) heterocycle, unsubstituted or substituted with 1-5 substituents independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$,
  l) $O(CO)NR^{10}R^{11}$, m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$; and $R^2$ is independently selected from H and:
1) $C_{1-6}$ alkyl,
2) $C_{3-6}$ cycloalkyl,
3) aryl, unsubstituted or substituted with 1-5 substituents independently selected from $R^4$,
4) heteroaryl, unsubstituted or substituted with 1-5 substituents independently selected from $R^4$,
5) heterocycle, unsubstituted or substituted with 1-5 substituents independently selected from $R^4$,
6) $(F)_pC_{1-3}$ alkyl,
7) halogen,
8) $OR^4$,
9) $O(CH_2)_sOR^4$,
10) $CO_2R^4$,
11) $(CO)NR^{10}R^{11}$,
12) $O(CO)NR^{10}R^{11}$,
13) $N(R^4)(CO)NR^{10}R^{11}$,
14) $N(R^{10})(CO)R^{11}$,
15) $N(R^{10})(CO)OR^{11}$,
16) $SO_2NR^{10}R^{11}$,
17) $N(R^{10})SO_2R^{11}$,
18) $S(O)_mR^{10}$,
19) CN,
20) $NR^{10}R^{11}$,
21) $N(R^{10})(CO)NR^4R^{11}$, and
22) $O(CO)R^4$;

$R^7$ is selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
 a) $C_{1-6}$ alkyl,
 b) $C_{3-6}$ cycloalkyl,
 c) aryl, unsubstituted or substituted with 1-5 substituents where the substituents are independently selected from $R^4$,
 d) heteroaryl, unsubstituted or substituted with 1-5 substituents independently selected from $R^4$,
 e) heterocycle, unsubstituted or substituted with 1-5 substituents independently selected from $R^4$,
 f) $(F)_pC_{1-3}$ alkyl,
 g) halogen,
 h) $OR^4$,
 i) $O(CH_2)_sOR^4$,
 j) $CO_2R^4$,
 k) $(CO)NR^{10}R^{11}$,
 l) $O(CO)NR^{10}R^{11}$,
 m) $N(R^4)(CO)NR^{10}R^{11}$,
 n) $N(R^{10})(CO)R^{11}$,
 o) $N(R^{10})(CO)OR^{11}$,
 p) $SO_2NR^{10}R^{11}$,
 q) $N(R^{10})SO_2R^{11}$,
 r) $S(O)_mR^{10}$,
 s) CN,
 t) $NR^{10}R^{11}$,
 u) $N(R^{10})(CO)NR^4R^{11}$, and
 v) $O(CO)R^4$; and 2) aryl or heteroaryl, unsubstituted or substituted with one or more substituents independently selected from:
 a) $C_{1-6}$ alkyl,
 b) $C_{3-6}$ cycloalkyl,
 c) aryl, unsubstituted or substituted with 1-5 substituents where the substituents are independently selected from $R^4$,
 d) heteroaryl, unsubstituted or substituted with 1-5 substituents independently selected from $R^4$,
 e) heterocycle, unsubstituted or substituted with 1-5 substituents independently selected from $R^4$,
 f) $(F)_pC_{1-3}$ alkyl,
 g) halogen,
 h) $OR^4$,
 i) $O(CH_2)_sOR^4$,
 j) $CO_2R^4$,
 k) $(CO)NR^{10}R^{11}$,
 l) $O(CO)NR^{10}R^{11}$,
 m) $N(R^4)(CO)NR^{10}R^{11}$,
 n) $N(R^{10})(CO)R^{11}$,
 o) $N(R^{10})(CO)OR^{11}$,
 p) $SO_2NR^{10}R^{11}$,
 q) $N(R^{10})SO_2R^{11}$,
 r) $S(O)_mR^{10}$,
 s) CN,
 t) $NR^{10}R^{11}$,
 u) $N(R^{10})(CO)NR^4R^{11}$, and
 v) $O(CO)R^4$;

$R^{10}$ and $R^{11}$ are independently selected from: H, $C_{1-6}$ alkyl, $(F)pC_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl, or morpholinyl, which is unsubstituted or substituted with 1-5 substituents independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;
X is C or S;
Y is O, $(R4)_2$, NCN, $NSO_2CH_3$ or $NCONH_2$, or Y is $O_2$ when X is S;

R5 is independently selected from H and:
1) $C_1$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
 a) $C_{1-6}$ alkyl,
 b) $C_{3-6}$ cycloalkyl,
 c) aryl, unsubstituted or substituted with 1-5 substituents independently selected from $R^4$,
 d) heteroaryl, unsubstituted or substituted with 1-5 substituents independently selected from $R^4$,
 e) heterocycle, unsubstituted or substituted with 1-5 substituents independently selected from $R^4$,
 f) $(F)_pC_{1-3}$ alkyl,
 g) halogen,
 h) $OR^4$,
 i) $O(CH_2)_sOR^4$,
 j) $CO_2R^4$,
 k) $(CO)NR^{10}R^{11}$,
 l) $O(CO)NR^{10}R^{11}$,
 m) $N(R^4)(CO)NR^{10}R^{11}$,
 n) $N(R^{10})(CO)R^{11}$, o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and,
v) $O(CO)R^4$;

2) aryl or heteroaryl, unsubstituted or substituted with one or more substituents independently selected from:
a) $C_{1-6}$ alkyl,
b) $C_{3-6}$ cycloalkyl,
c) aryl, unsubstituted or substituted with 1-5 substituents independently selected from $R^4$,
d) heteroaryl, unsubstituted or substituted with 1-5 substituents independently selected from $R^4$,
e) heterocycle, unsubstituted or substituted with 1-5 substituents independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$;

3) $C_{1-6}$ alkyl,
4) $C_{3-6}$ cycloalkyl,
5) heterocycle, unsubstituted or substituted with 1-5 substituents independently selected from $R^4$,
6) $(F)_pC_{1-3}$ alkyl,
7) halogen,
8) $OR^4$,
9) $O(CH_2)_sOR^4$,
10) $CO_2R^4$,
11) $(CO)NR^{10}R^{11}$,
12) $O(CO)NR^{10}R^{11}$,
13) $N(R^4)(CO)NR^{10}R^{11}$,
14) $N(R^{10})(CO)R^{11}$,
15) $N(R^{10})(CO)OR^{11}$,
16) $SO_2NR^{10}R^{11}$,
17) $N(R^{10})SO_2R^{11}$,
18) $S(O)mR^{10}$,
19) CN,
20) $NR^{10}R^{11}$,
21) $N(R^{10})(CO)NR^4R^{11}$, and,
22) $O(CO)R^4$, or two $R^5$ attached to the same carbon form the substituent =O, such that $C(R^5)_2$ may be C=O,
where the number of $R^5$ substituents that are not H, can range from zero to three;
$R^6$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with
a) $(F)_pC_{1-3}$ alkyl,
b) halogen,
c) $OR^4$,
d) $O(CH_2)_sOR^4$,
e) $CO_2R^4$,
f) $(CO)NR^{10}R^{11}$,
g) $O(CO)NR^{10}R^{11}$,
h) $N(R^4)(CO)NR^{10}R^{11}$,
i) $N(R^{10})(CO)R^{11}$,
j) $N(R^{10})(CO)OR^{11}$,
k) $SO_2NR^{10}R^{11}$,
l) $N(R^{10})SO_2R^{11}$,
m) $S(O)_mR^{10}$,
n) CN,
o) $NR^{10}R^{11}$,
p) $N(R^{10})(CO)NR^4R^{11}$, and
q) $O(CO)R^4$;

G_J is selected from: N, $C(R^5)$, $C=C(R^5)$, $N-C(R^5)_2$, C=N, $C(R^5)-C(R^5)_2$, $C(R^5)-N(R^6)$, and $N-N(R^6)$;

Q-T is selected from: $C(R^5)_2-C(R^5)_2$, $C(R^5)=C(R^5)$, $N=C(R^5)$, $C(R^5)=N$, N=N, $N(R^6)$, $C(R^5)_2-(C=O)$, $N(R^6)-(C=O)$, and $C(R^5)_2-N(R^6)$;

$R^3$ is independently selected from H, substituted or unsubstituted $C_1-C_3$ alkyl, CN, F, $OR^4$ and $CO_2R^4$;

p is 0 to 2q+1, for a substituent with q carbons; m is 0, 1 or 2; s is 1, 2 or 3;

"heteroaryl" means a stable 5- to 7-membered monocyclic- or stable 9- to 10-membered fused bicyclic heterocyclic ring system which contains an aromatic ring, any ring of which may be saturated, partially saturated, or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring;

"heterocycle" means a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring;

or a pharmaceutically acceptable salt or diastereomer thereof.

2. The compound of claim 1 of the Formula Ia:

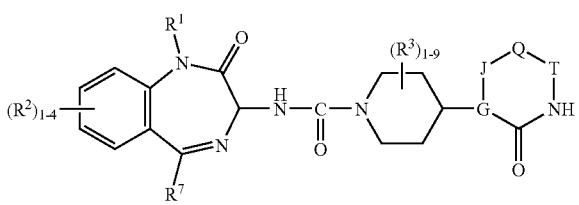

Ia or a pharmaceutically acceptable salt or diastereomer thereof.

3. The compound of claim 1 of the Formula Ib

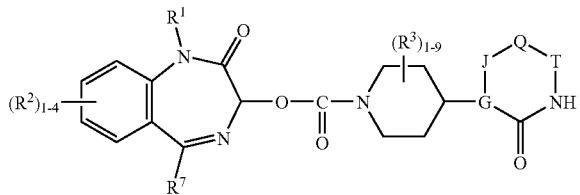

or a pharmaceutically acceptable salt or diastereomer thereof.

4. The compound of claim 1, wherein:

$R^1$ is selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents independently selected from $R^4$,
   d) heteroaryl, unsubstituted or substituted with 1-5 substituents independently selected from $R^4$,
   e) heterocycle, unsubstituted or substituted with 1-5 substituents independently selected from $R^4$,
   f) $(F)_p C_{1-3}$ alkyl,
   g) halogen,
   h) $OR^4$,
   i) $O(CH)_s OR^4$,
   j) $COR^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_m R^{10}$,
   s) CN,
   t) $NR^{10}R^{11}$,
   u) $N(R^{10})(CO)NR^4R^{11}$, and
   v) $O(CO)R^4$; and
2) aryl or heteroaryl, unsubstituted or substituted with one or more substituents independently selected from:
   a) $C_{1-6}$ alkyl,
   b) C3-6 cycloalkyl,
   c) aryl, unsubstituted or substituted with 1-5 substituents where the substituents are independently selected from $R^4$,
   d) heteroaryl, unsubstituted or substituted with 1-5 substituents independently selected from $R^4$,
   e) heterocycle, unsubstituted or substituted with 1-5 substituents independently selected from $R^4$,
   f) $(F)_p$C1-3 alkyl,
   g) halogen,
   h) $OR^4$,
   i) $O(CH_2)_s OR^4$,
   j) $CO2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)Mr^{10}$,
   s) CN,
   t) $NR^{10}R^{11}$,
   u) $N(R^{10})(CO)NR^4R^{11}$, and
   v) $O(CO)R^4$; and R2 is independently selected from H and:
1) $C_{1-6}$ alkyl,
2) $C_{3-6}$ cycloalkyl,
3) aryl, unsubstituted or substituted with 1-5 substituents independently selected from $R^4$,
4) heteroaryl, unsubstituted or substituted with 1-5 substituents independently selected from $R^4$,
5) heterocycle, unsubstituted or substituted with 1-5 substituents independently selected from $R^4$,
6) $(F)_p C_{1-3}$ alkyl,
7) halogen,
8) $OR^4$,
9) $O(CH_2)_s OR^4$,
10) $CO_2R^4$,
11) $(CO)NR^{10}R^{11}$,
12) $O(CO)NR^{10}R^{11}$,
13) $N(R^4)(CO)NR^{10}R^{11}$,
14) $N(R^{10})(CO)R^{11}$,
15) $N(R^{10})(CO)OR^{11}$,
16) $SO_2NR^{10}R^{11}$,
17) $N(R^{10})SO_2R^{11}$,
18) $S(O)_m R^{10}$,
19) CN,
20) $NR^{10}R^{11}$,
21) $N(R^{10})(CO)NR^4R^{11}$, and
22) $O(CO)R^4$;

$R^7$ is selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents independently selected from $R^4$,
   e) heterocycle, unsubstituted or substituted with 1-5 substituents independently selected from $R^4$,
   f) $(F)_p C_{1-3}$ alkyl,
   g) halogen,
   h) $OR^4$,
   i) $O(CH_2)_s OR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_m R^{10}$,
   s) CN,
   t) $NR^{10}R^{11}$,
   u) $N(R^{10})(CO)NR^4R^{11}$,
   v) $O(CO)R^4$; and 2) aryl or heteroaryl, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents independently selected from $R^4$,
   d) heteroaryl, unsubstituted or substituted with 1-5 substituents independently selected from $R^4$,
   e) heterocycle, unsubstituted or substituted with 1-5 substituents independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10}) SO_{02} R^{11}$,
   r) $S(O)_m R^{10}$,
   s) $CN$,
   t) $NR^{10}R^{11}$,
   u) $N(R^{10})(CO)NR^4 R^{11}$, and
   v) $O(CO)R^4$;

$R^{10}$ and $R^{11}$ are independently selected from: H, $C_{1-6}$ alkyl, $(F)pC_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl and morpholinyl, which is unsubstituted or substituted with 1-5 substituents independently selected from $R^4$ $R^4$ is independently selected from: H, $C_{1-6}$ alkyl, $(F)pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;
G_J is N and Q-T is $C(R^5)_2$-$C(R^5)_2$, or,
G-J is N and Q-T is $C(R^5)=C(R^5)$, or,
G-J is N and Q-T is $N=C(R^5)$, or,
G-J is N and Q-T is $C(R^5)=N$, or,
G-J is N and Q-T is $N=N$, or,
G-J is $C=C(R^5)$ and Q-T is $N(R^6)$, or,
G-J is N and Q-T is $C(R^5)_2$-$(C=O)$, or,
G-J is $N-C(R^5)_2$ and Q-T is $C(R^5)_2$-$C(R^5)_2$, or,
G-J is $C=C(R^5)$ and Q-T is $C(R^5)=C(R^5)$, or,
G-J is $C=C(R^5)$ and Q-T is $C(R^5)=N$, or,
G-J is $C=C(R^5)$ and Q-T is $N=C(R^5)$, or,
G-J is $C=N$ and Q-T is $C(R^5)=C(R^5)$, or,
G-J is $N-C(R^5)_2$ and Q-T is $C(R^5)_2$-$(C=O)$, or,
G-J is $C(R^5)$-$C(R^5)2$ and Q-T is $N(R^6)$-$(C=O)$, or,
G-J is $C(R^5)$-$C(R^5)_2$ and Q-T is $C(R^5)_2$-$C(R^5)_2$, or,
G-J is $C(R^5)$-$C(R^5)_2$ and Q-T is $C(R^5)_2$-$N(R^6)$, or,
G-J is $C(R^5)$-$N(R^6)$ and Q-T is $C(R^5)_2$-$C(R^5)_2$, or,
G-J is $C(R^5)$-$C(R^5)2$ and Q-T is $N=C(R^5)$, or,
G-J is $N-C(R^5)_2$ and Q-T is $C(R^5)_2$-$N(R^6)$, or,
G-J is $N$-$N(R^6)$ and Q-T is $C(R^5)_2$-$C(R^5)_2$, or,
G-J is $N-C(R^5)_2$ and Q-T is $N=C(R^5)$;

$R^5$ is independently selected from H and:
   1) $C_1$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
      a) $C_{1-6}$ alkyl,
      b) $C_{3-6}$ cycloalkyl,
      c) aryl, unsubstituted or substituted with 1-5 substituents independently selected from $R^4$,
      d) heteroaryl, unsubstituted or substituted with 1-5 substituents independently selected from $R^4$,
      e) heterocycle, unsubstituted or substituted with 1-5 substituents independently selected from $R^4$,
      f) $(F)_p C_{1-3}$ alkyl,
      g) halogen,
      h) $OR^4$,
      i) $O(CH_2)_s OR^4$,
      j) $CO_2 R^4$,
      k) $(CO)NR^{10}R^{11}$,
      l) $O(CO)NR^{10}R^{11}$,
      m) $N(R^4)(CO)NR^{10}R^{11}$,
      n) $N(R^{10})(CO)R^{11}$,
      o) $N(R^{10})(CO)OR^{11}$,
      p) $SO_2 NR_{10} R_{11}$,
      q) $N(R^{10}) SO_2 R^{11}$,
      r) $S(O)_m R^{10}$,
      s) $CN$,
      t) $NR^{10}R^{11}$,
      u) $N(R^{10})(CO)NR^4 R^{11}$, and,
      v) $O(CO)R^4$;
   2) aryl or heteroaryl, unsubstituted or substituted with one or more substituents independently selected from:
      a) $C_{1-6}$ alkyl,
      b) $C_{3-6}$ cycloalkyl,
      c) aryl, unsubstituted or substituted with 1-5 substituents independently selected from $R^4$,
      d) heteroaryl, unsubstituted or substituted with 1-5 substituents independently selected from $R^4$,
      e) heterocycle, unsubstituted or substituted with 1-5 substituents independently selected from $R^4$,
      f) $(F)_p C_{1-3}$ alkyl,
      g) halogen,
      h) $OR^4$,
      i) $O(CH_2)_s OR^4$,
      j) $CO_2 R^4$,
      k) $(CO)NR^{10}R^{11}$,
      l) $O(CO)NR^{10}R^{11}$,
      m) $N(R^4)(CO)NR^{10}R^{11}$,
      n) $N(R^{10})(CO)R^{11}$,
      o) $N(R^{10})(CO)OR^{11}$,
      p) $SO_2 NR^{10}R^{11}$,
      q) $N(R^{10}) SO_2 R^{11}$,
      r) $S(O)_m R^{10}$,
      s) $CN$,
      t) $NR^{10}R^{11}$,
      u) $N(R^{10})(CO)NR^4 R^{11}$, and
      v) $O(CO)R^4$;
   3) $C_{1-6}$ alkyl,
   4) $C_{3-6}$ cycloalkyl,
   5) aryl, unsubstituted or substituted with 1-5 substituents independently selected from $R^4$,
   6) heteroaryl, unsubstituted or substituted with 1-5 substituents independently selected from $R^4$,
   7) heterocycle, unsubstituted or substituted with 1-5 substituents independently selected from $R^4$,
   8) $(F)_p C_{1-3}$ alkyl,
   9) halogen,
   10) $OR^4$,
   11) $O(CH_2)_s OR^4$,
   12) $CO_2 R^4$,
   13) $(CO)NR^{10}R^{11}$, 14) O(CO)NR$^{10}$R$^{11}$,
15) N(R$^4$)(CO)NR$^{10}$R$^{11}$,
16) N(R$^{10}$)(CO)R$^{11}$,
17) N(R$^{10}$)(CO)OR$^{11}$,
18) SO$_2$NR$^{10}$R$^{11}$,
19) N(R$^{10}$) SO$_2$R$^{11}$,
20) S(O)mR$^{10}$,
21) CN,
22) NR$^{10}$R$^{11}$,
23) N(R$^{10}$)(CO)NR$^4$R$^{11}$, and
24) O(CO)R$^4$, or two R$^5$ attached to the same carbon form the substituent =O, such that C(R$^5$)2 may be C=O, where the number of R$^5$ substituents that are not H, can range from zero to three;

R$^3$ is independently selected from H, substituted or unsubstituted C$_1$-C$_3$ alkyl, CN and CO$_2$R$^4$;

p is 0 to 2q+1, for a substituent with q carbons; m is 0 to 2; s is 1 to 3;

or a pharmaceutical acceptable salt or diastereomer thereof.

5. A compound selected from:

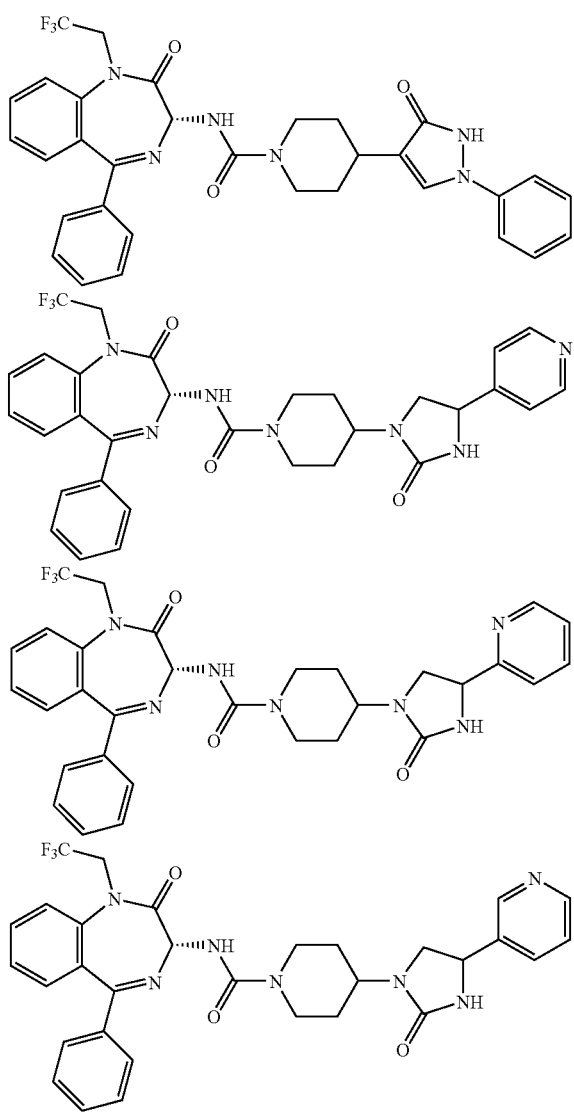

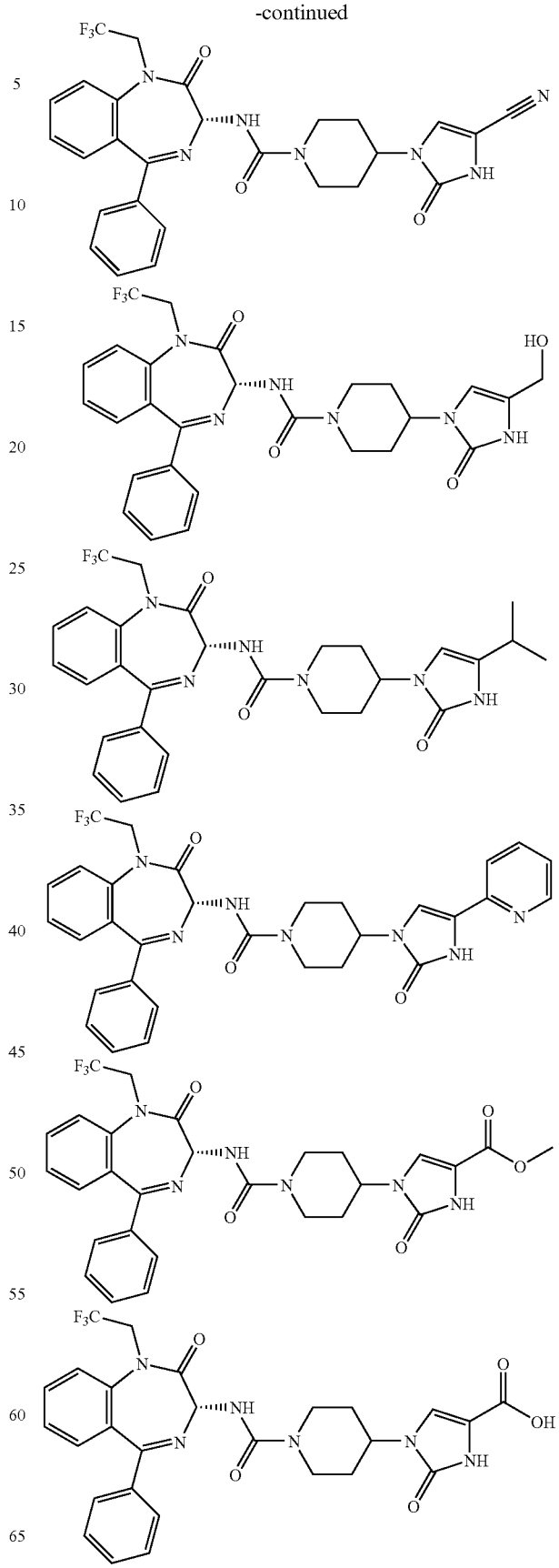

75
-continued
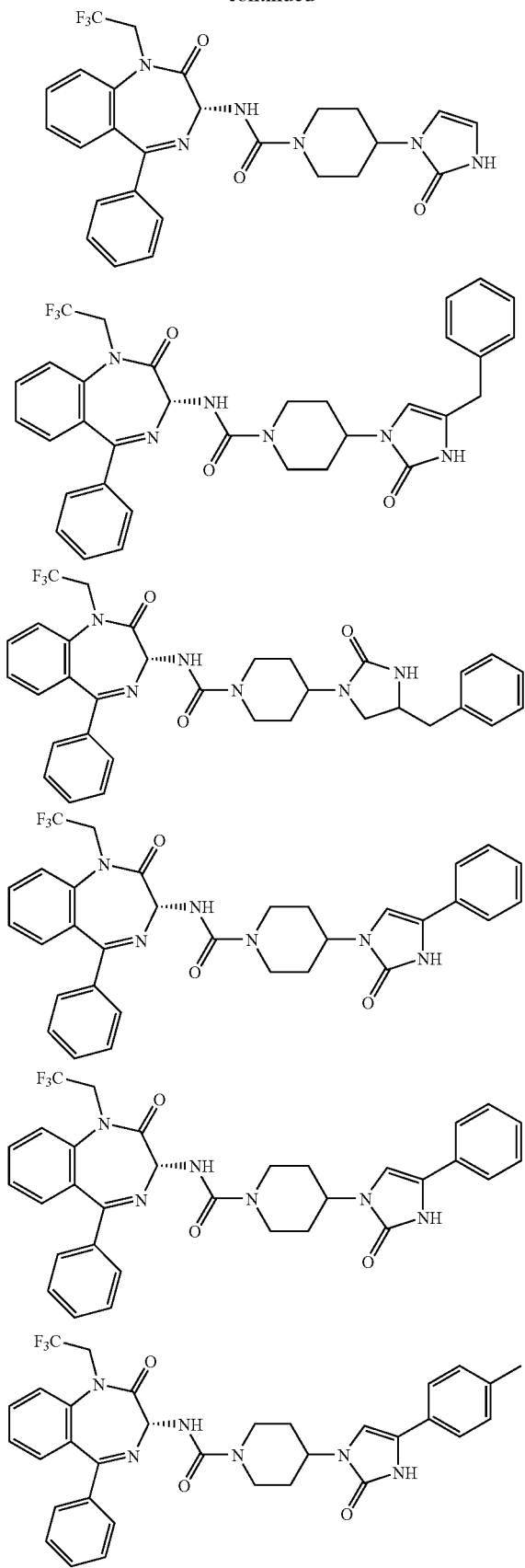
76
-continued
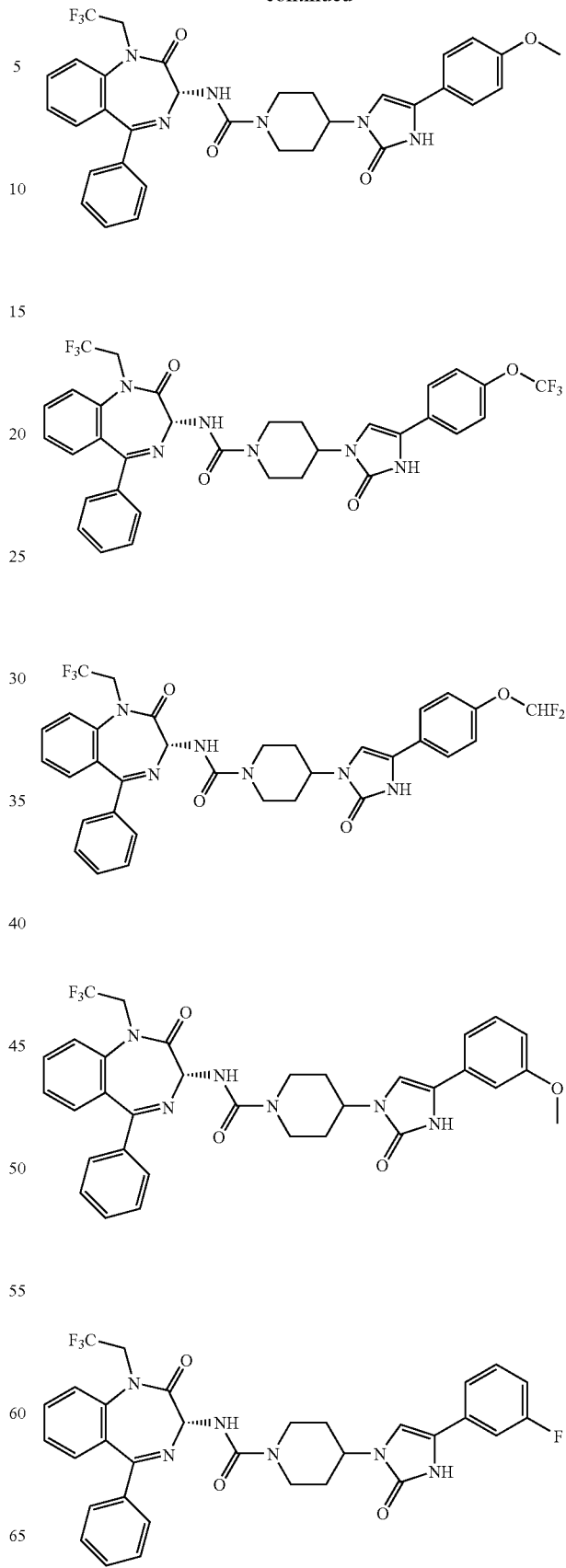

-continued
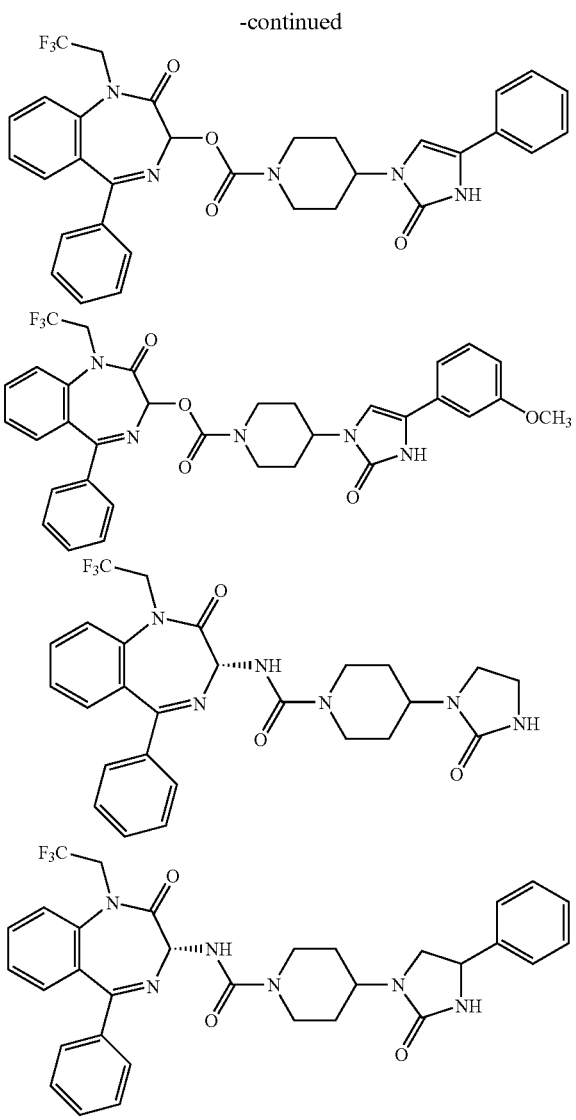
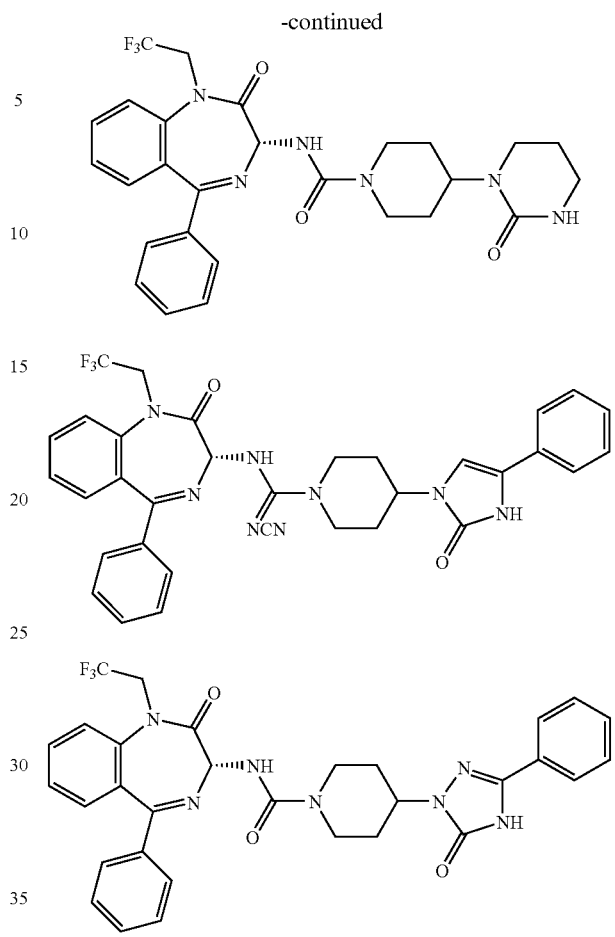
or a pharmaceutically acceptable salt or diastereomer thereof.
6. A pharmaceutical composition which comprises an inert carrier and the compound of claim 1.
* * * * *